(12) United States Patent
Kent et al.

(10) Patent No.: US 7,957,155 B2
(45) Date of Patent: Jun. 7, 2011

(54) SYSTEM FOR ATTACHING A SUBSTANTIALLY THREE-DIMENSIONAL STRUCTURE TO A SUBSTANTIALLY TWO-DIMENSIONAL STRUCTURE

(75) Inventors: Harold B. Kent, Portola Valley, CA (US); Steven T. Kent, Portola Valley, CA (US)

(73) Assignee: Medconx, Inc., Santa Clara, CA (US)

( * ) Notice: Subject to any disclaimer, the term of this patent is extended or adjusted under 35 U.S.C. 154(b) by 841 days.

(21) Appl. No.: 11/377,818

(22) Filed: Mar. 15, 2006

(65) Prior Publication Data

US 2006/0278072 A1 Dec. 14, 2006

Related U.S. Application Data

(60) Provisional application No. 60/662,455, filed on Mar. 15, 2005.

(51) Int. Cl.
*H05K 7/06* (2006.01)

(52) U.S. Cl. ....... 361/767; 29/602.1; 336/185; 336/199; 361/761

(58) Field of Classification Search ................. 29/602.1, 29/606, 832; 336/199, 200, 205, 185, 220; 361/761, 767, 777
See application file for complete search history.

(56) References Cited

U.S. PATENT DOCUMENTS

| | | | | |
|---|---|---|---|---|
| 3,721,932 | A | * | 3/1973 | Fierstien et al. ............... 336/65 |
| 3,936,776 | A | * | 2/1976 | Sundquist ..................... 333/202 |
| 5,604,471 | A | * | 2/1997 | Rattila et al. .................. 333/202 |
| 6,511,463 | B1 | | 1/2003 | Wood et al. |

FOREIGN PATENT DOCUMENTS

| | | |
|---|---|---|
| JP | 61-121390 | 7/1986 |
| JP | 06-101791 | 4/1994 |
| JP | 2003-8204 | 1/2003 |
| JP | 2003-027535 | 1/2003 |
| JP | 2003-535304 | 11/2003 |

OTHER PUBLICATIONS

Extended EP Search Report for EP 06738703.5, based on PCT/US2006/009670, corresponding to this U.S. Appl. No. 11/377,818.

* cited by examiner

*Primary Examiner* — A. Dexter Tugbang
*Assistant Examiner* — Livius R Cazan
(74) *Attorney, Agent, or Firm* — Jones Day

(57) ABSTRACT

A method and system for transporting a fluid, gas, semi-solid, cryogen, or particulate matter, or combination thereof, between a three-dimensional structure and a substantially two-dimensional structure is disclosed. A system and method for electrically coupling a three-dimensional structure to a substantially two dimensional structure is also disclosed.

25 Claims, 27 Drawing Sheets

SYSTEM FOR ATTACHING A SUBSTANTIALLY THREE-DIMENSIONAL STRUCTURE TO A SUBSTANTIALLY TWO-DIMENSIONAL STRUCTURE

CROSS-REFERENCE TO RELATED APPLICATION

This application claims priority to U.S. Provisional Application No. 60/662,455, filed on Mar. 15, 2005, the disclosure of which is incorporated herein by reference in its entirety.

FIELD

This disclosure generally relates to attachment methods and more particularly to a method of soldering a substantially three dimensional structure to a substantially two dimensional structure. The three dimensional structure can be a medical catheter and the two dimensional structure can be a Printed Circuit Board. The three dimensional structures can transport different media such as electrical current, liquids, gases, and particulates.

BACKGROUND

Currently, electrical catheters consist of a hollow tube surrounding fine wires that are individually stripped, either by hand, by a laser, by bead blasting, by chemical etching, or various other methods, and terminated into bulky connectors and solder-cups. In an effort to reduce the size of the catheter, wires have been getting progressively smaller and smaller. As the wires get smaller they also become physically weaker. These weaker wires tend to break and become difficult to handle during the assembly process required for high conductor count catheters. Large numbers of very thin conductors running axially along a catheter are also notorious for being un-flexible and have a tendency to get tangled, twisted, nicked, kinked, skived (exposing the electrical conductor), broken or get in the way of any guiding or steering wires that may be in operation, thus creating electrical shorts and opens. With an increase in the number of conductors, space limitation enhances the electrical issues. Assembly time also increases as more wires are manually fed through the length of the catheter. Reworking and repairing the catheters becomes time consuming, and, in some cases, impossible without destroying the catheter.

A more desirable situation for modern catheters would be one that incorporates a system for easy termination of an ever increasing number of conductors and that allows for quick, reliable, and or redundant solder joints. Having a mechanical structure designed for flexibility would also aid in reducing field and assembly failures. Ideally, a new catheter termination system would also enable a production operator to easily switch between leaded and lead free solder without sacrificing production speed or capability.

SUMMARY

A method and system for transporting a fluid, gas, semi-solid, cryogen, or particulate matter, or combination thereof, between a three-dimensional structure and a substantially two-dimensional structure are disclosed. A system and method for electrically coupling a three-dimensional structure to a substantially two dimensional structure are also disclosed.

DETAILED DESCRIPTION

Figure 1:
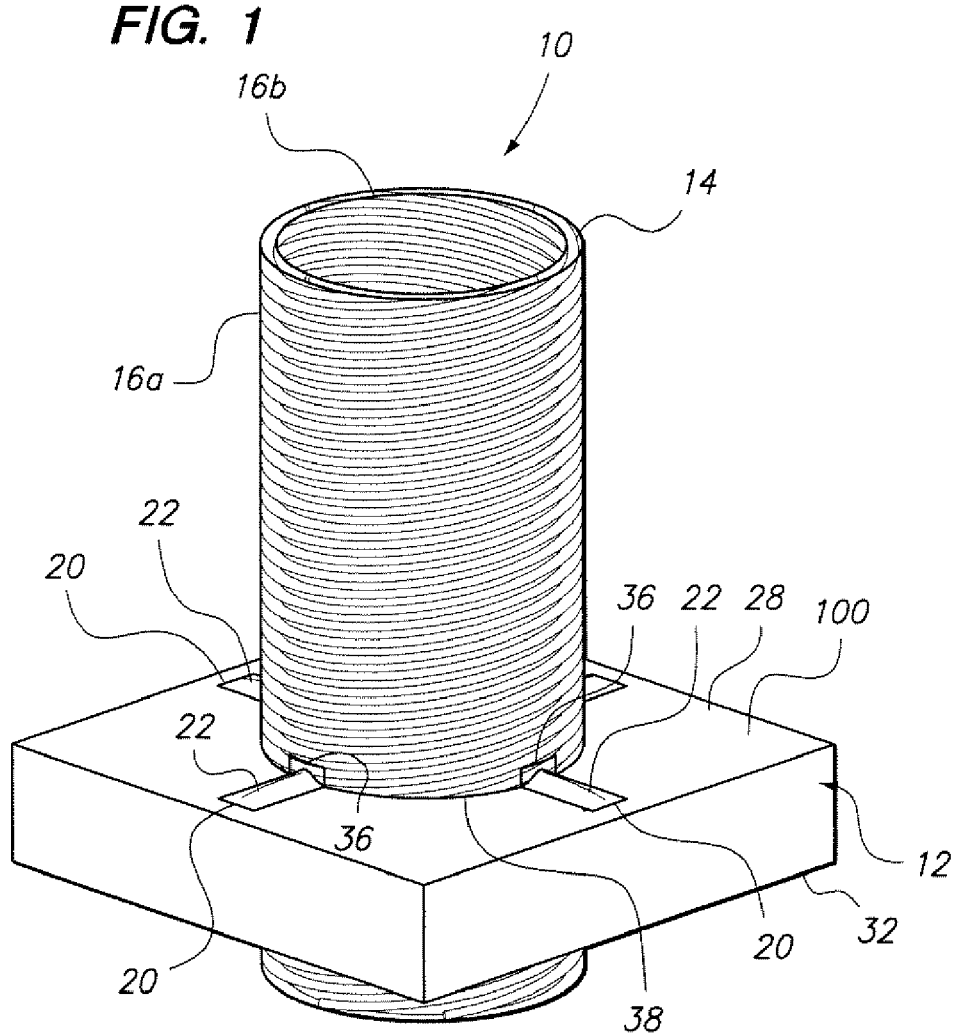
FIG. 1 is a perspective view of an example system.
Figure 2:
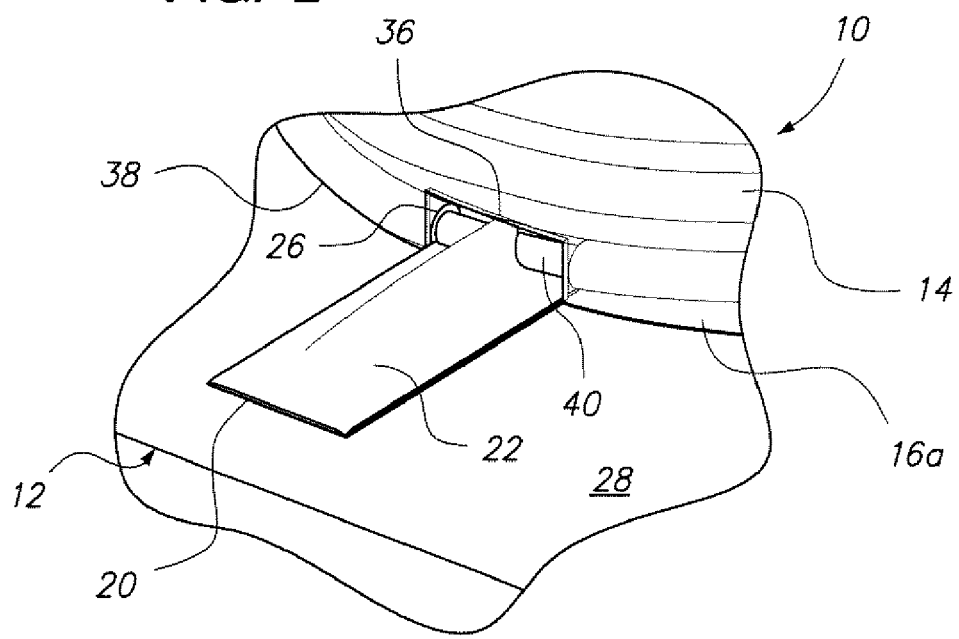
FIG. 2 is an expanded view of the example system of FIG. 1.

A system for soldering a substantially three dimensional structure to a substantially two dimensional substrate is described. An example of the system has a coil of elements and a substrate designed to receive the coil. In some examples the coil lies in a groove formed on one of the surfaces of a dielectric substrate, such as a printed circuit board ("PCB"). A connection pad or transfer point is disposed on a surface of the dielectric substrate and is designated to receive the coil. The connection pad is adjacent to the groove or the path of the coil such that a connection can be made between an element of the coil and the connector pad. The coil element has a coating that is removed at the location of the connection between the coil and the connection pad.

Furthermore, the system can include a heat transfer pad in thermal communication with the connection pad in order to transfer heat to the coil of elements and the connection material on the pad without physically contacting or contaminating the pad or the connection material. Typically, the coil of elements has multiple conductors wound therein and the substrate has a plurality of connection pads or transfer points for conductors in the coil. It is possible to vary the number of connection pads in order to provide redundant connections for safety and reliability or to allow for easier access to tightly coiled elements. The coil of elements may be wound around a hollow tube, wound over a fiber optic element, or wrapped around any other suitable substrate. The shape of the "coil structure" can be formed by any means. A sheath can also cover the wires for further protection or aesthetic reasons.

The coil of elements can also have varying pitch to increase or decrease the apparent rigidity and flexibility of the resultant system at predetermined points without having to use different materials. This change of pitch also allows for the convenient locating of access points to the conductors contained in the coil and the dielectric substrate. This makes it easier to terminate each transfer point within the complex structure of the coil of elements.

Additionally, the system can include attachments to multiple dielectric substrates. The coil of elements and the substrate can also be formed so that each substrate will only interact with the coil of elements in a predetermined location and orientation. The coil of elements may also be used for structural reinforcement of the system, which is especially useful when combined with pull wires or other such steering devices. Any given element within the coil need not be electrically conductive. The core of an element may be dissolvable, and once dissolved, leave a hollow core element which would then be capable of carrying a variety of liquid, gaseous, or semi-solid materials, or a combination of materials thereof.

FIGS. 1-4 depict an example system for electrically coupling a three dimensional structure to a substantially two dimensional structure. The two dimensional structure is shown as a dielectric substrate 12 that has a thickness. The thickness may be created by a single material or by the combination of a series of substrates that are connected to one another. The three-dimensional structure is created by a coil of elements 10, which in this case, is a coil of wires 14. The coil of wires 10 is positioned between an outer sheath 16a and an inner sheath 16b. In this example, the sheaths are shown as being a transparent, flexible material.

The coil of elements 10 includes a plurality of wires 14 which are spaced one after another within the coil such that a first wire is positioned adjacent a second wire which is positioned adjacent a third wire, etc. The coil of elements 10 is coupled to the dielectric substrate 12 at connection points which are defined by a contact pad 20 and connection solder 22. The contact pad 20 is a pad of conductive material that is positioned on a surface of the dielectric substrate 12. The contact pad 20 could be recessed into the surface of the dielectric substrate 12, or could be positioned on top 28 of the surface 12. It could be created through plating or any other known means for attaching a conductive material to a dielectric substrate. Connection solder 22 is positioned on top of the contact pad 20.

In the example shown in FIGS. 1-4, four contact pads 20 are evenly spaced around a mounting hole 38, which is a through-hole positioned in the dielectric substrate 12. Mounting hole 38 is a cylindrical hole having a round cross-section and is sized and shaped to receive the coil of elements 10 therethrough. The connection points are designed to couple to the wires 14 within the coil of elements 10 to establish an electrical connection between the contact pad 20 and the associated wire 14. In order to allow coupling of the wires 14 within the coil of elements 10 to substrate 12, the outer sheath 16a of the coil of elements 10 is cut away in an area of the coil of elements 10 where the contact pad 20 can mate with a preselected wire 14. In addition, a protective sheathing 26, such as a plastic coating, on the wire 14 is cut away in the area of the contact pad 20.

Once the coil of elements 10 is positioned inside the mounting hole 38, a heating element, not shown, can be applied to each contact pad 20 in order to heat the solder 22 positioned thereon. When the contact pad 20 is heated with the heating element, such as a soldering iron, the connection solder 22 will flow to the wire 14 and wick onto the wire 14, thereby establishing an electrical and mechanical connection between the solder, contact pad 20 and the wire 14.

In FIG. 1, four wires 14 are shown positioned within the coil of elements 10. The connection points on the dielectric substrate 12 are positioned in order to mate with each one of the wires 14 on an upper surface 28 of the dielectric substrate 12. While the present example shows a cylindrical coil of elements 10 having four wires 14, it should be noted that the coil of elements 10 can have any shape including cylindrical, rectangular, polygonal, oval, or any other type of shape that could be positioned in a mounting hole. In addition, any number of wires and any number of connection points may be utilized in connection with this example, the example not being limited to the exact configuration shown.

Figure 3:
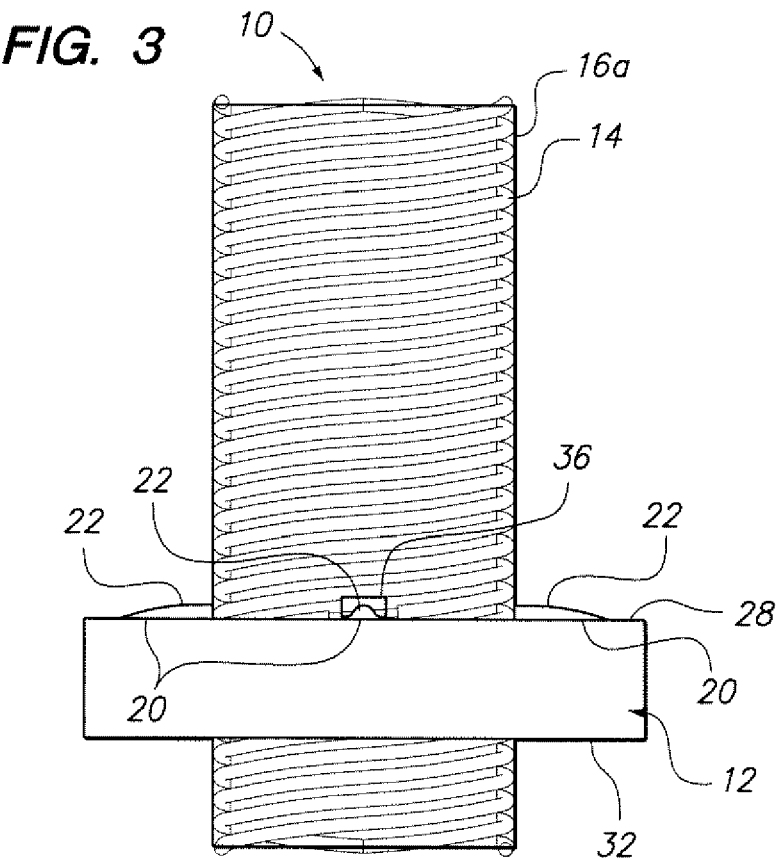
FIG. 3 is a side elevation view of the example system of FIG. 1.
Figure 4:
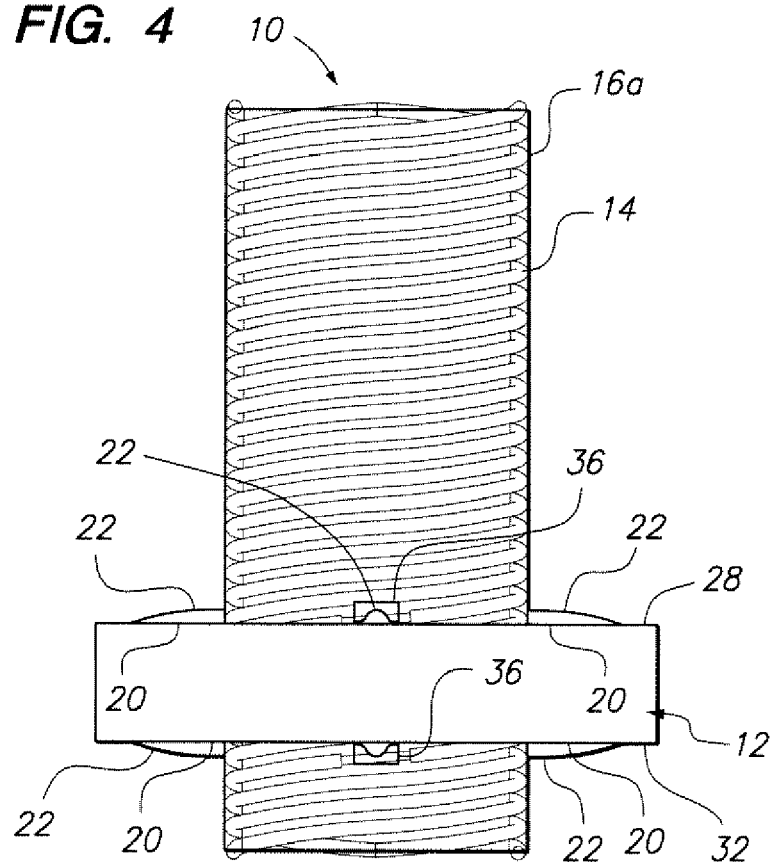
FIG. 4 is a side elevation view of the example system of FIG. 1 with additional electrical connectors.

FIG. 3 shows the coil of elements 10 being connected to the dielectric substrate 12 along a top surface 28 of the dielectric substrate 12. FIG. 4 depicts a similar example, but in this example, the coil of elements 10 is coupled to both the top and bottom surfaces 28, 32 of the dielectric substrate 12. In this example, connection points are disposed on both the top and bottom surfaces 28, 32 of the dielectric substrate 12. The outer sheath 16a of the coil of elements 10 has openings 36 cut into the sheath such that wires 14 within the coil of elements 10 may be exposed for connection to both the top and bottom surfaces 28, 32 of the dielectric substrate 12.

The example of FIG. 4 provides additional mechanical stability to the system by having the coil of elements 10 coupled to the substrate 12 in more than one plane. In addition, FIG. 4 provides for additional electrical connections between the wires 14 and the contact pads 20. This may provide protective redundancy within the system. This, may allow electricity to travel from one point in a wire to another across the substrate 12 without requiring an additional via (or hole) to be positioned in the substrate 12. Lastly, as previously discussed, the connection points or solder points between the coiled elements 10 and the dielectric substrate 12 assist in improving the mechanical strength of the system for electrically coupling the three-dimensional structure 10 to a substantially two-dimensional structure 12.

The two dimensional structure in these examples is the top surface 28 of the dielectric substrate 12 or the bottom surface 32 of the dielectric substrate 12. While the dielectric substrate 12 has a thickness such that it is actually a three-dimensional structure, the contact pad 20 is considered the two-dimensional structure that the coil of elements 10 is coupled to. The coil of elements 10 is the three-dimensional structure that is being coupled to the two-dimensional structure of the substrate 12. The word "substantially" is used herein to refer to the two-dimensional structure, which, in some examples, is the top surface 28 of the dielectric substrate 12 because it will be recognized that the contact pad 20 and solder 22 themselves do provide more than a strict two-dimensional structure. However, the structure is substantially two-dimensional according to the definition of two-dimensional structure utilized herein.

As discussed above, FIG. 1 illustrates an exemplary method of attaching a coil of elements 10 in the form of a tubular structure to a dielectric substrate 12. It should be understood that the tubular structure need not be round or even hollow, as can be seen in FIGS. 22-31 described below. Connection pads 20 are disposed on the outer planar surfaces of the dielectric substrate 12. Each connection pad 20 can optionally be in electrical communication or thermal communication with other structures on the dielectric substrate 12, such as electrical traces (not shown). Connection material 22 rests on the top of the connection pads 20 and can be either added before the tubular structure or after the tubular structure is inserted into the mounting hole 38. The connection pads 20 are usually arranged in a radial pattern around the mounting hole 38. Once the tubular structure has been inserted into the mounting hole 38, connection material 22 bonds individual wires 14 contained within the tubular structure to individual connection pads 20 on the dielectric substrate 12. This bonding is usually done through the use of heat from a heating element which can be either a separate device or contained within the dielectric substrate 12. By attaching the tubular structure to the top 28 and to the bottom 32 of the dielectric substrate 12, a robust mechanical retention is generated at the same time as electrical communication is established.

Generally, the tubular structure contains patterns of wires 14 disposed between an inside layer 16a and an outside layer 16b. While the material of the tube provides for electrical isolation between various wires 14, each wire 14 can also be coated in an isolative material with a sheathing 26, or otherwise to either ensure or enhance the dielectric properties of the tube material. The dielectric materials 26 covering any given wire 14 will only be removed to the minimum extent possible so as to maximize the structural integrity of the tubular structure.

Figure 5:
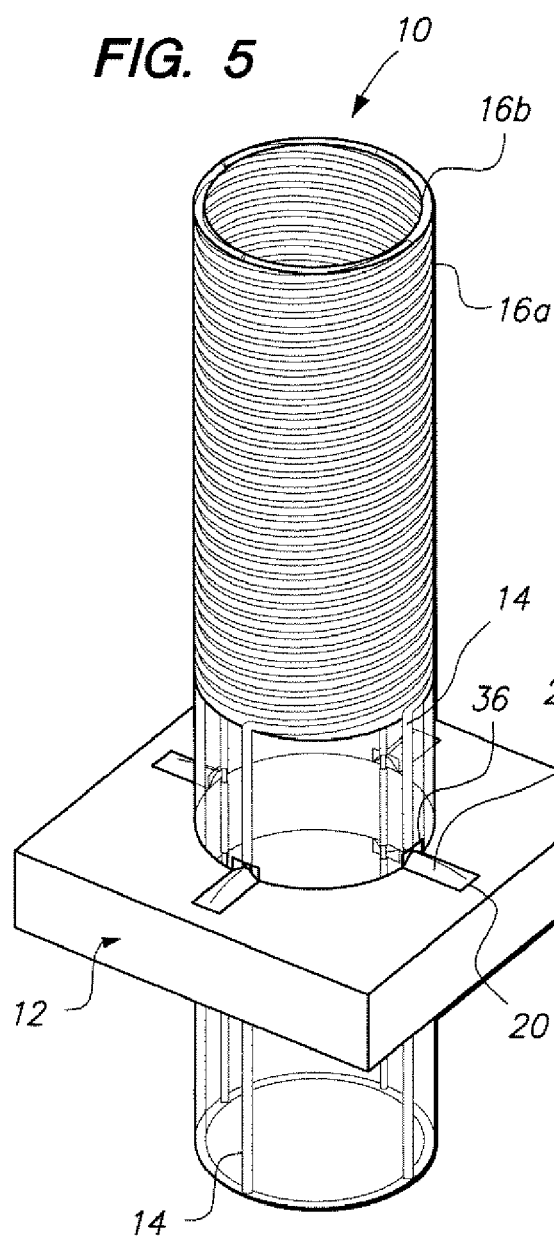
FIG. 5 is a perspective view of a second example system.
Figure 6:
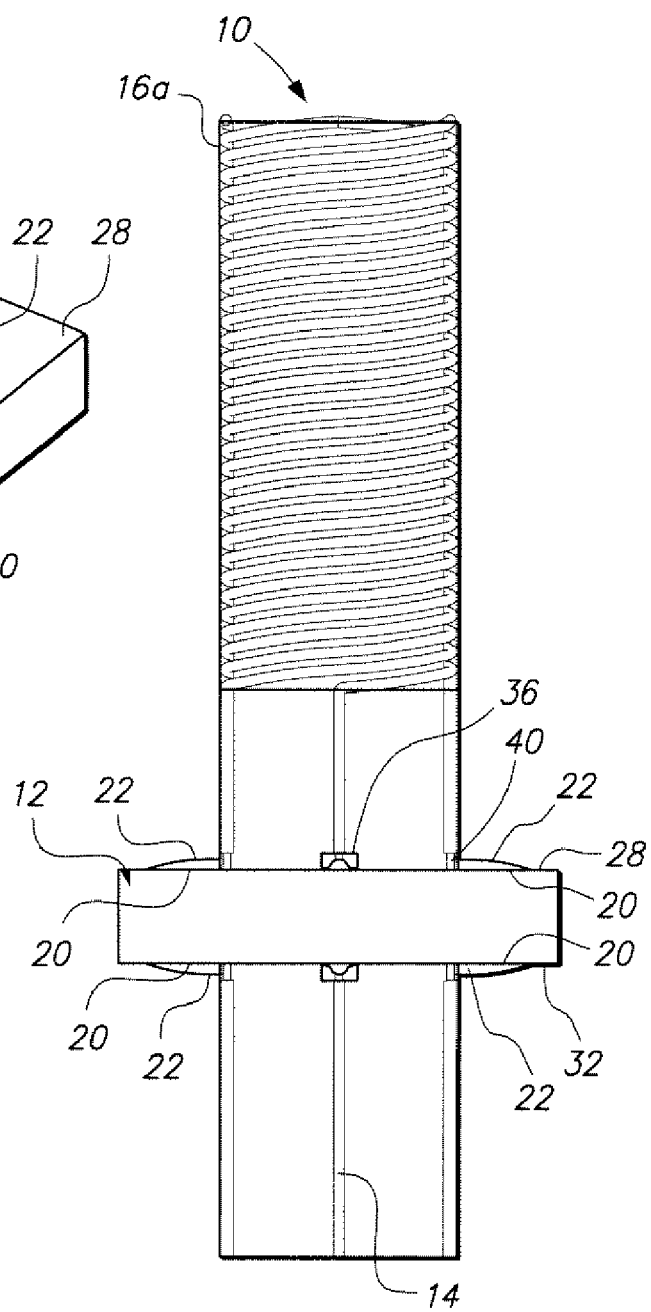
FIG. 6 is a side elevation view of the example system of FIG. 5.

In the previously described examples of FIGS. 1-4, the coil of elements 10 included a series of wires 14 that were cylindrically wound around the inner sheath 16b of coil of elements 10. FIGS. 5 and 6 depict an alternative example similar to the examples discussed in FIGS. 1-4.

In FIGS. 5 and 6, the coil of elements 10 includes an upper portion of wires 34 that are wound around an inner sheath 16b, but at the point where the coil of elements 10 is positioned in the mounting hole of the dielectric substrate 12, the wires 14 change direction and, instead of being wound around the inner sheath 16b, they longitudinally extend along the length of the coil of elements 10 between the inner sheath 16b and the outer sheath 16a. The connection method previously described in connection with FIG. 4 is utilized for connecting the wires 14 to the contact pads 20 with the connection solder 22. A hole 36 is cut in the outer sheath 16a in order to allow the solder 22 to couple to the wire 14 that is positioned inside the sheath 16a. The wire 14 is stripped of any protective material 26 around the conductive portion of the wire 14. In general, the wire will have a plastic outer sheathing 26 and either part, or all of this, protective plastic sheathing 26 may be cutaway in the vicinity of the contact pad 20.

Generally, the tubular structure contains patterns of wires disposed between an inside layer 16b and an outside layer 16a. While the material of the tube provides for electrical isolation between various wires 14, each wire 14 can also be coated in an isolative material to either ensure or enhance the dielectric properties of the tube material. Preferably the dielectric materials covering any given wire will only be removed to the minimum extent possible so as to maximize the structural integrity of the tubular structure. FIGS. 5-10 show some patterns and structures that accomplish these goals.

Each method can be accomplished using a variety of techniques ranging from chemical etching to laser stripping to mechanical ablation. Many different methods and patterns can be used, and the ones shown are merely for illustrative purposes. wires 14 can be stripped axially either in strips or following the curve of the coil. wires 14 can be stripped such that the wires 14 are hanging in free space. Wires 14 can also be stripped so that only a portion of their total inner core is exposed. There can exist multiple strip zones along the length of the tubular structure. Each zone can be of a different strip type and can expose only certain selected wires.

As shown in FIG. 6, the outer sheath 16*a* may be cut at points that mate with both the top and bottom surfaces 28, 32 of the dielectric substrate 12. As previously discussed in connection with FIG. 4, the use of connection points on both the top and bottom surfaces 28, 32 of the dielectric substrate 12 provides additional mechanical stability to the joint between the three-dimensional structure of the coil of elements 10 and the two-dimensional structure of the surface connection for the wire 14.

Figure 7:
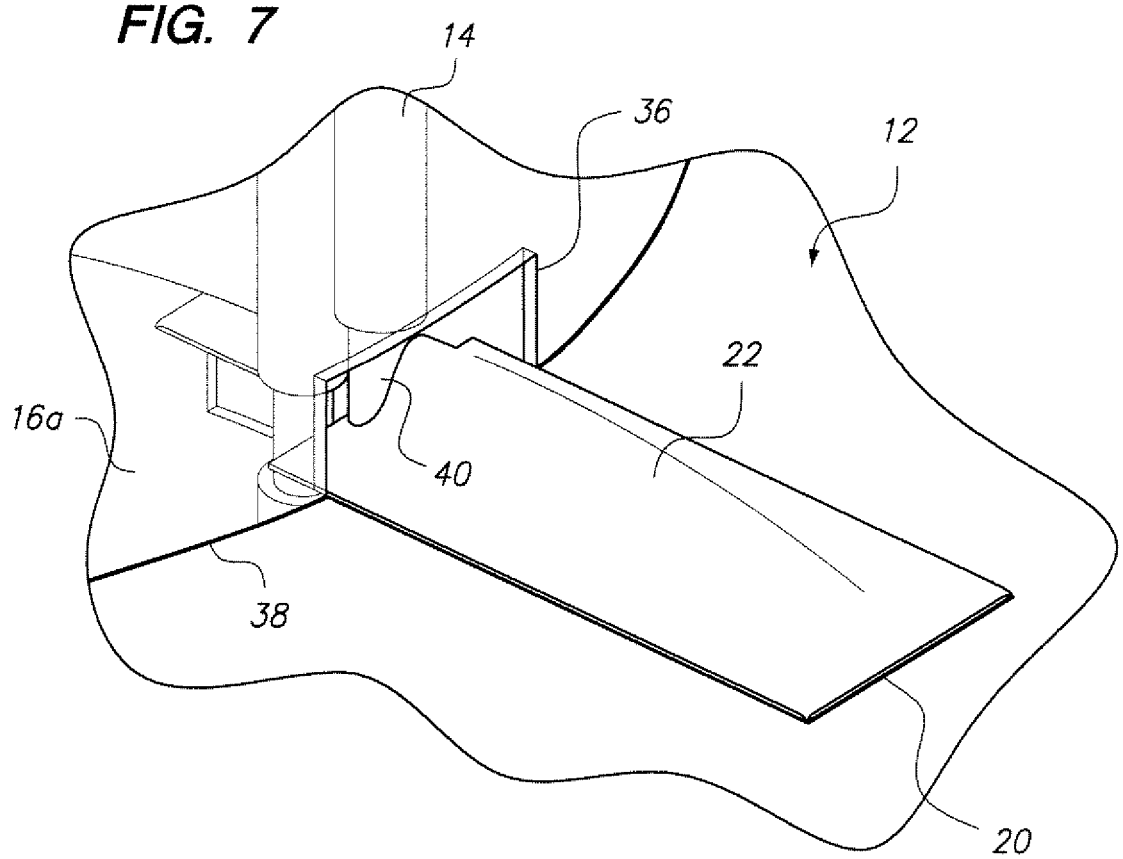
FIG. 7 is an expanded view of the example system of FIG. 5 with a fully stripped wire.
Figure 8:
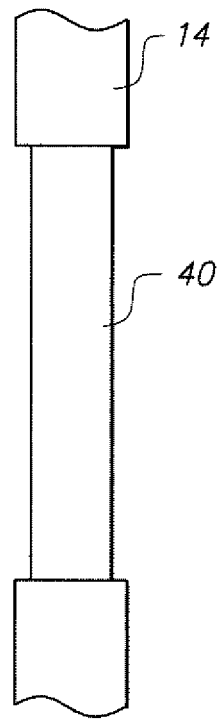
FIG. 8 is a side elevation view of a fully stripped wire.

FIGS. 7-10 depict two examples of the way the protective sheathing 26 may be removed from a wire 14 such that the wire can couple to the solder 22. In FIGS. 7 and 8, the wire 14 is stripped around the entire circumference of the inner conductive core 40. The outer material 26, because it is not conductive, will not allow the wire to mate with the solder 22. For this reason, it is necessary to strip the protective sheathing 26 of the wire 14. As shown in FIG. 7, the solder 22 on the contact pad 20 mates with the inner conductive material 40 of the wire 14. In order to establish both an electrical connection between the contact pad 20 and the conductive material 40 of the wire 14 and a mechanical connection between the contact pad 20, solder 22 and wire 14 such that the wire 14 is coupled to the top surface 28 of the dielectric substrate 12.

Figure 9:
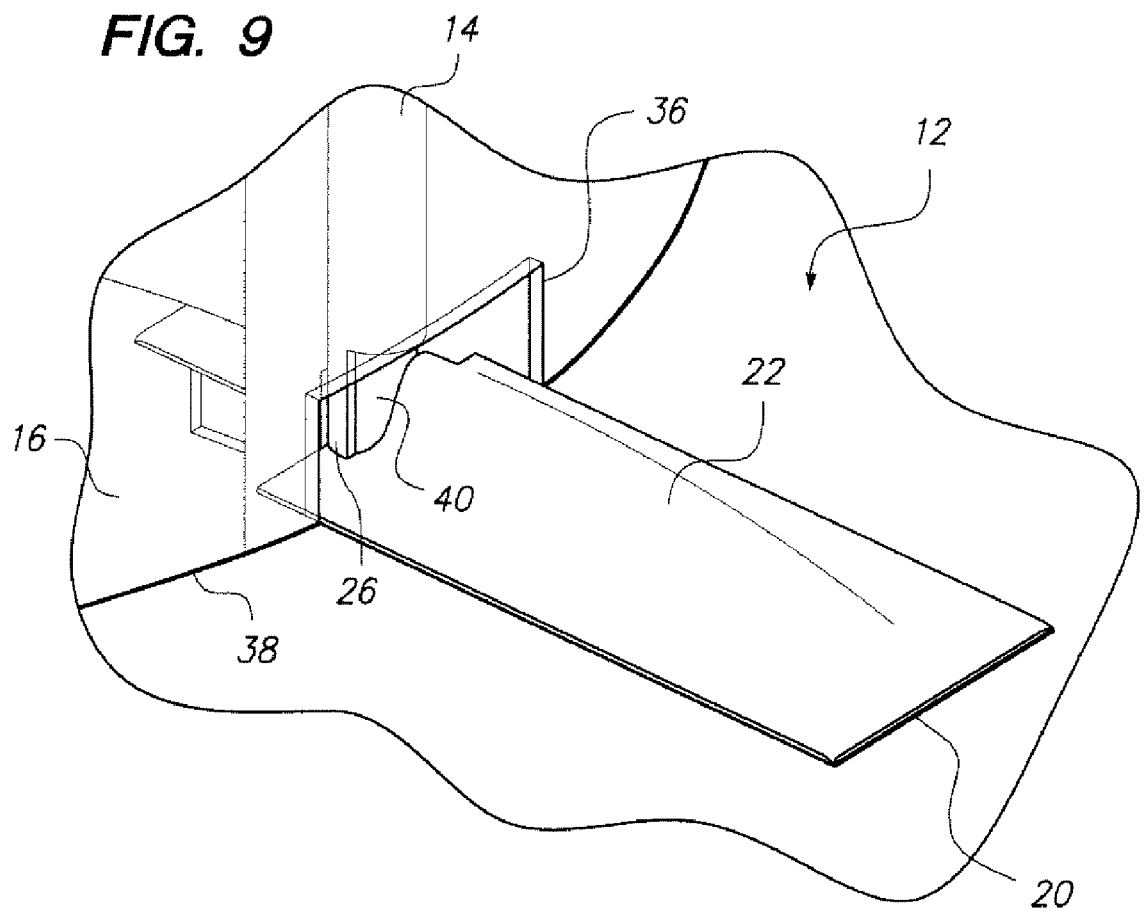
FIG. 9 is an expanded view of the example system of FIG. 5 with a partially stripped wire.
Figure 10:
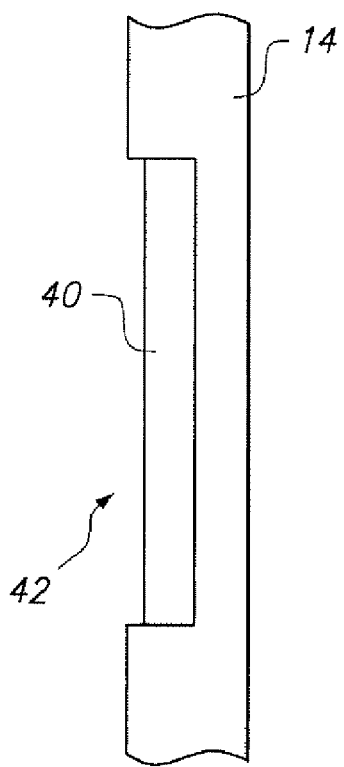
FIG. 10 is a side elevation view of a partially stripped wire.

FIGS. 9 and 10 are similar to FIGS. 7 and 8 except for, in this example, the wire 14 is only stripped of the plastic outer sheathing 26 on one side of the wire 14 in the vicinity of the opening 36 that is cut in the outer sheathing 16*a* of the coil of elements 10. In this example, a window 42 is created in the wire 14 such that the conductive material of the wire 14 is exposed for connection to the connection solder 22. The method of applying the solder 22 to the conductive member 40 of the wire 14 is the same as that previously discussed in connection with FIGS. 1-4. The heating element (not shown) may be applied to the contact pad 20 in order to heat the solder 22. Solder 22 then flows towards the conductive material 40 of the wire 14 and wicks onto the conductive material 40 in order to couple the solder 22 to the conductive material 40 of the wire 14, thereby establishing both an electrical and mechanical connection with the wire 14.

Figure 11:
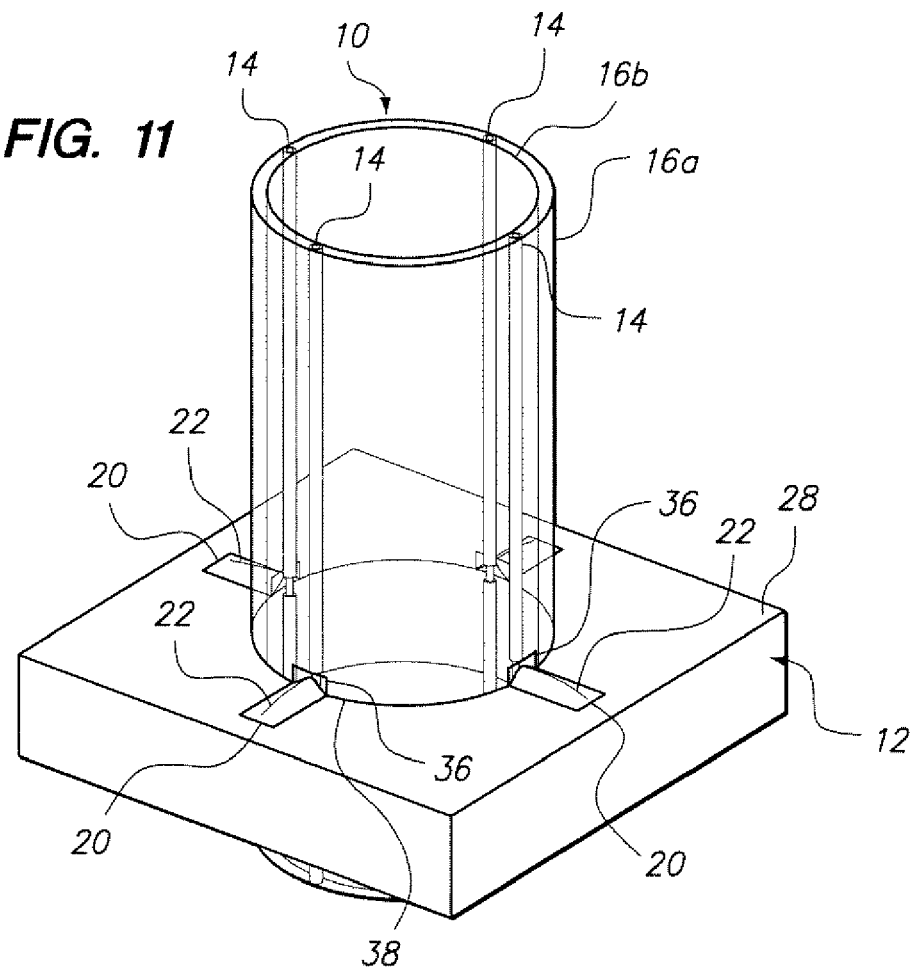
FIG. 11 is a perspective view of a third example system.
Figure 12:
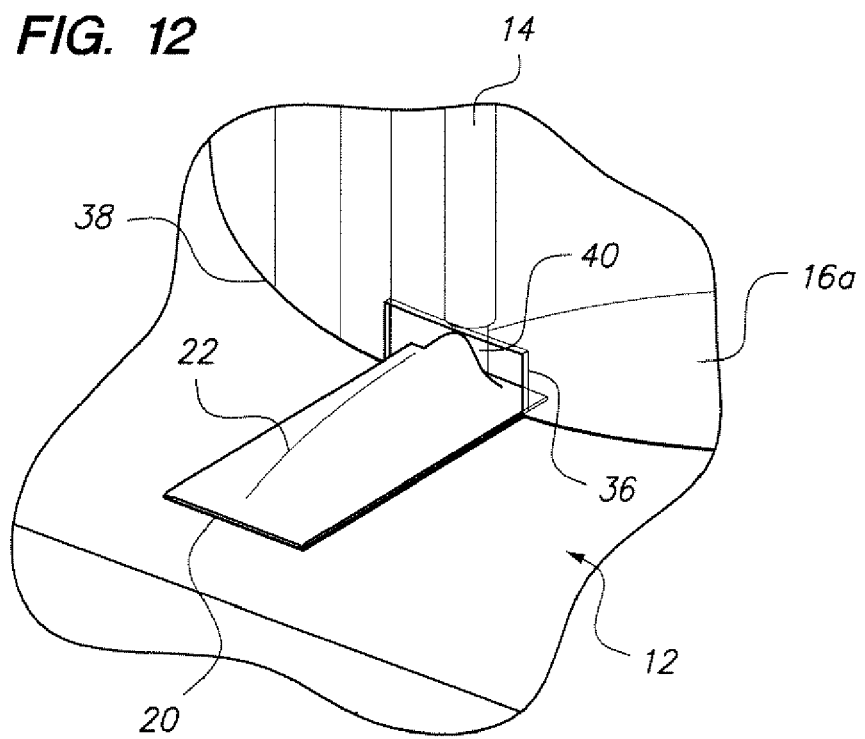
FIG. 12 is an expanded view of the example system of FIG. 11.

FIGS. 11-12 show how the pattern of wires 14 need not be coiled to still be effective. Coiling the wires 14 around a tubular structure allows for some advantages though. Chief among them is that coiled wires 14 are more flexible and less prone to breaking then straight wires. This means that the flexibility and apparent durometer of any given tubular structure can be changed from changing the coiled wires 14 to straight wires, or just by changing the type of coil being used.

FIGS. 11 and 12 depict another example of a system for electrically coupling a three-dimensional structure to assist a substantially two-dimensional structure. In this example, the wires 40 of the coil of elements 10 extend axially along the length of the coil of elements 10. The coil in this example, is created by the combination of the outer and inner sheaths 16*a*, 16*b*. The wires 14 are not wound around the inner core 16*b*. Instead, they extend axially between the inner and outer sheaths 16*a*, 16*b*. The coil of elements 10 is again cylindrical and positioned in a mounting hole 38 that is defined in a dielectric substrate 12. The dielectric substrate 12 includes contact pads 20 and connection solder 22 positioned on each of the contact pads 20. The coil of element 10 is positioned through the hole 38 and the dielectric substrate 12 and the wires 14 of the coil of elements 10 are coupled to the contact pads 20 on the top surface 28 of the dielectric substrate 12 according to any of the methods previously discussed. As with the prior examples, the outer sheath 16*a* is cut away to form an opening 36 through which the solder 22 can communicate with the respective wire 14.

FIG. 12 shows a close-up of the connection between the solder 22 and the conductive material 40 of the wire 14. In this example, the plastic sheathing 26 around the wire 14 has been removed around the circumference of the wire, as previously discussed in connection with FIG. 8, in the vicinity of the contact pad 20 and the hole 36 positioned in the outer sheath of the coil of elements 10.

Figure 13:
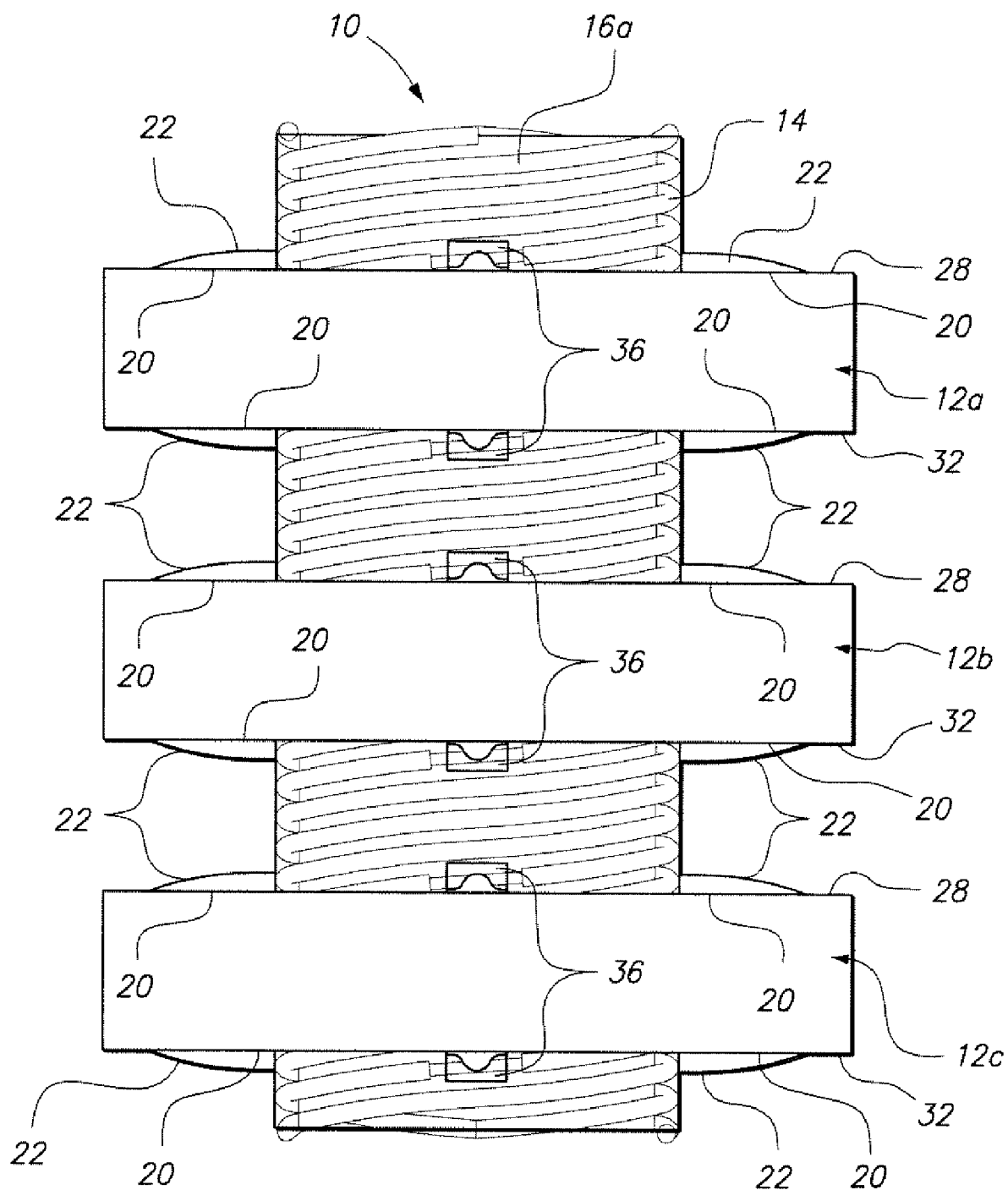
FIG. 13 is a side elevation view of a fourth example system.
Figure 14:
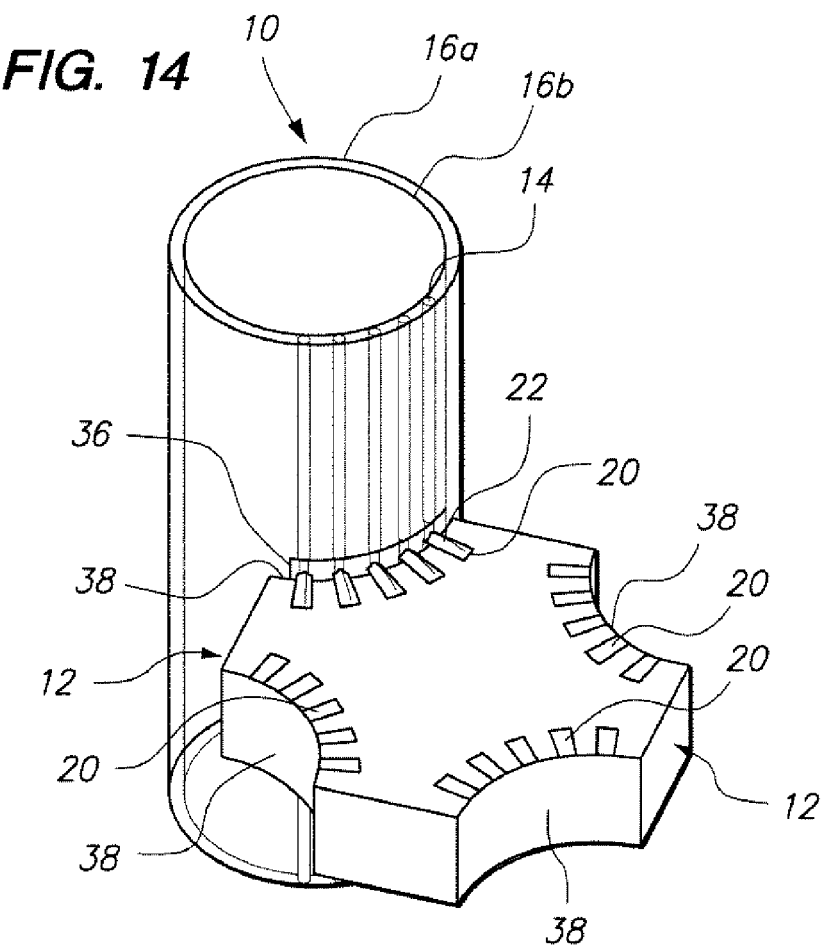
FIG. 14 is a perspective view of a fifth example system.

FIG. 13 is an example similar to the previously disclosed examples where the coil of elements 10 comprises a plurality of wires 14 that are wound around an inner sheath 16*b*. An outer sheath 16*a* holds the wires 14 between the inner and outer sheaths to establish a cylindrical body which makes up the coil of elements 10. In this example, three dielectric substrates are disclosed including a top dielectric substrate 12*a*, a middle dielectric substrate 12*b*, and a lower dielectric substrate 12*c*. The wires 14 within the coil of elements 10 are coupled to the upper and lower surfaces 28, 32 of the dielectric substrates in the manner previously discussed in connection with the prior examples. This includes the use of a conductive contact pad 20 disposed on a surface of the dielectric substrate 12 with a connection solder 22 being coupled to each contact pad 20. In addition, the coil of elements outer sheath 16*a* has a hole 36 cut into the sheath in the vicinity of each contact pad 20 such that a wire 14 within the coil of elements 10 can be coupled to each of the contact pads 20 via the connection solder 22.

The example shown in FIG. 13 can be used for a system where a large number of wires are positioned in the coil of elements 10 such that, for example, each wire could be coupled to one or more of the substrates 12*a*, 12*b*, 12*c*, either one or more times. With a greater number of wires 14, the number of connection points would be reduced since only a limited number of contact pads 20 and connection solder 22 are provided. This example would allow for redundancy between the wire connections such that a single wire could be coupled to a dielectric substrate 12 a number of times. In addition, this example could be utilized to improve the mechanical strength of the system because a greater number of solder joints provides a greater mechanical strength and retention. In addition, this example could be utilized in order to couple a wire to a variety of different substrates. By coupling the wires 14 to the substrates 12, additional vias and connectors can be avoided within the system.

As discussed above, FIG. 13 shows multiple dielectric substrates disposed along the length of a singular tubular structure. Each dielectric substrate 12*a*, 12*b*, 12*c* can be used singly or each can be in electrical communication with another dielectric substrate 12. Having multiple substrates allows for an increase in mechanical alignment for the tubular structure, as well as an increase in the available area for connection pads 20 in high wire count coils.

FIGS. 14-17 depict an alternative example of the system for electrically coupling a three-dimensional structure to a substantially two-dimensional structure. In this example, the dielectric substrate 12 includes a plurality of holes or passageways 38 in the form of cut-outs on the corners of the dielectric substrate 12. Instead of having the hole 38 disposed through the center of the dielectric substrate 12, in this example, the dielectric substrate 12 has the corners cut out and the coil of elements 10 is positioned partially into one of the corners. While this example shows a part of the coil of elements 10 being inserted into the openings 38 in the dielectric substrate 12, the size and shape of the coil of elements 10 and the size and shape of the dielectric substrate 12 and the holes 38 of the dielectric substrate 12 could be modified such that a greater proportion of the coil of elements 10 is positioned within the corner passageway or hole 35 of the dielectric substrate 12, the example not being limited to the depicted dimensional characteristics. While in the prior examples, the contact pads 20 were disposed around a circular hole in the dielectric substrate 12. In this example, the contact pads 20 are disposed around the cutaway opening 38 in the corners of the dielectric substrate 12. In this example, the cutaways 38 in the dielectric substrate 12 are arcuate such that the contact pads 20 are spaced along the edge of the arcuate opening for connection with a coil of elements 10 positioned adjacent the arcuate opening. The coil of elements 10 includes a plurality of wires 14 that extend axially along the length of the coil of elements 10 between the inner 16b and outer 16a sheaths of the coil of elements 10.

Figure 15:
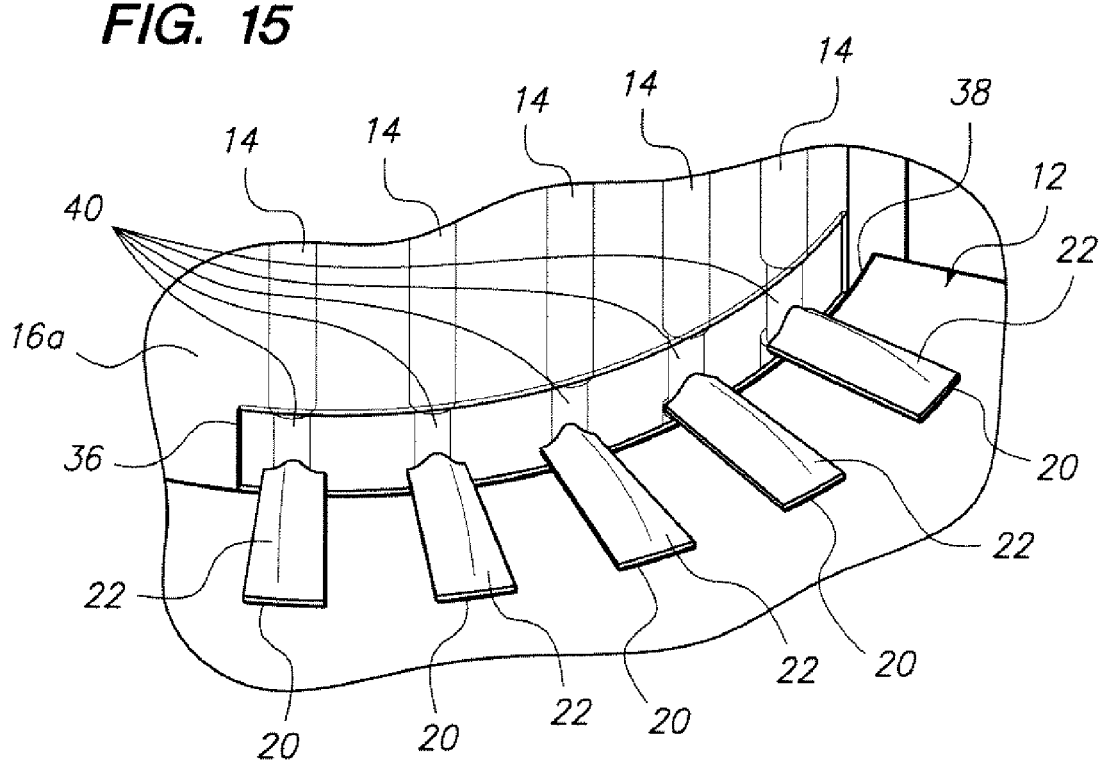
FIG. 15 is an expanded view of the example system of FIG. 14.

As shown in FIG. 15, the wires 14 may be stripped of their plastic outer sheathing 26 to reveal the conductive material 40 of the wires 14 and this conductive material 40 may be coupled to each contact pad 20 in the manner previously described in the prior examples, by melting a solder 22 disposed on each contact pad 20 such that the solder 22 wicks onto each wire 14 and establishes electrical communication and mechanical communication between the solder 22 and the conductive portion 40 of the wires 14.

Figure 16:
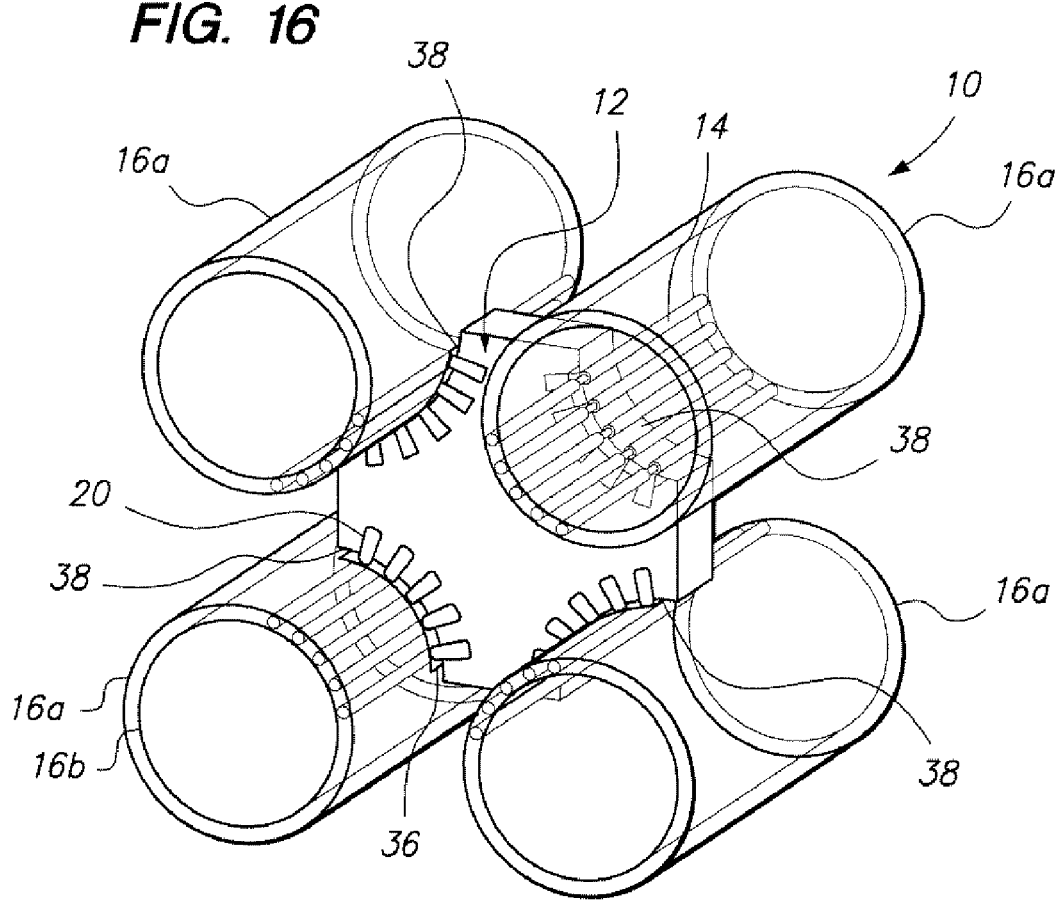
FIG. 16 is a perspective, partially-transparent view of the example system of FIG. 14 with three additional coils of elements.
Figure 17:
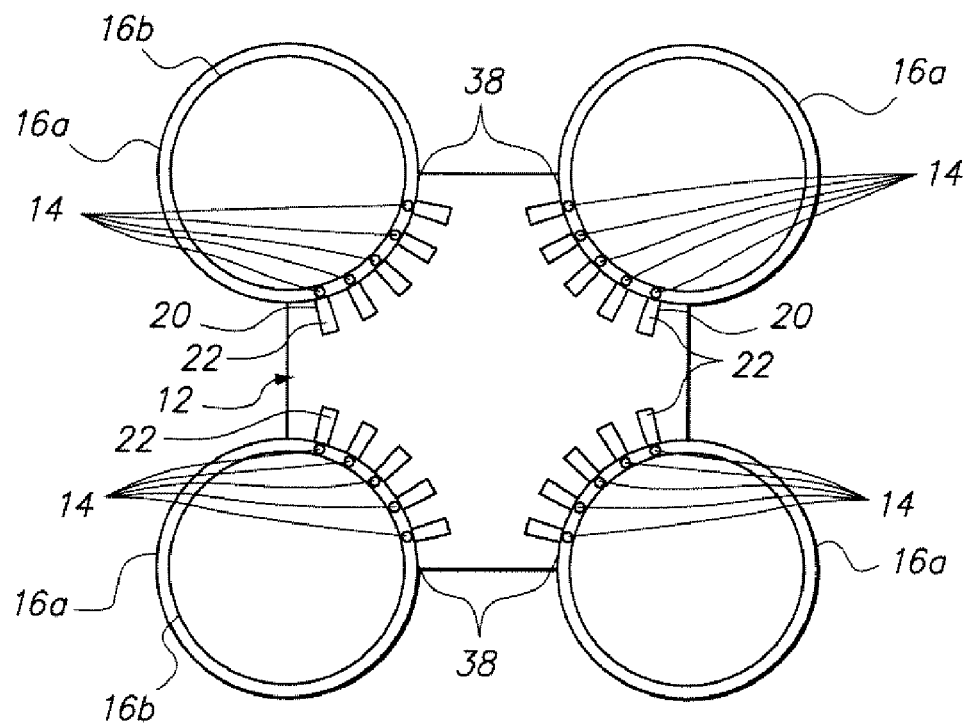
FIG. 17 is a side elevation view of the example system of FIG. 14 with three additional coils of elements.

FIGS. 16 and 17 show views of how a plurality of coil of elements 10 may be connected to the dielectric substrate 12 that has the corners cut out to form corner passageways. In the examples shown in FIGS. 16 and 17, four coils of elements 10 are coupled to the dielectric substrate 12, with one coil being positioned in each arcuate opening on the corners of the dielectric substrate 12. Each coil of elements 10 includes wires 14 that extend axially along the length of the coil of elements 10 and the wires 14 may be joined to the contact pads 20 in a manner previously discussed in connection with FIG. 15. The use of the dielectric substrate 12 to join the four coils of elements 10 together helps to provide mechanical stability between the four coils of elements 10. While not shown, the coils of elements 10 may be joined to both an upper and a lower surface 28, 32 of the dielectric substrate 12, if so desired. While the coil of elements 10 in this example is shown as including axially extending wires 14, it should be recognized by those skilled in the art that the coil of elements 10 could include wires 14 that are wound around the inner sheath 16b instead of longitudinally or axially extending wires 14 as shown in the figures.

FIGS. 14-17 show a similar arrangement of dialectic substrates 12 as that shown in FIG. 13. However, instead of the tubular structure passing through the core of a dielectric substrate 12, the tubular structure 10 passes though an edge of the dielectric substrate 12. Such an arrangement would allow for easier integration in compact clamshell type hand pieces as each dielectric substrate 12 would have only a portion of the tubular structure 10 to interact with at any given time. It is also easy to add multiple tubular structures 10 to a single dielectric substrate 12 when the tubular structures 10 are disposed at the edges of the dielectric substrate 12.

Figure 18:
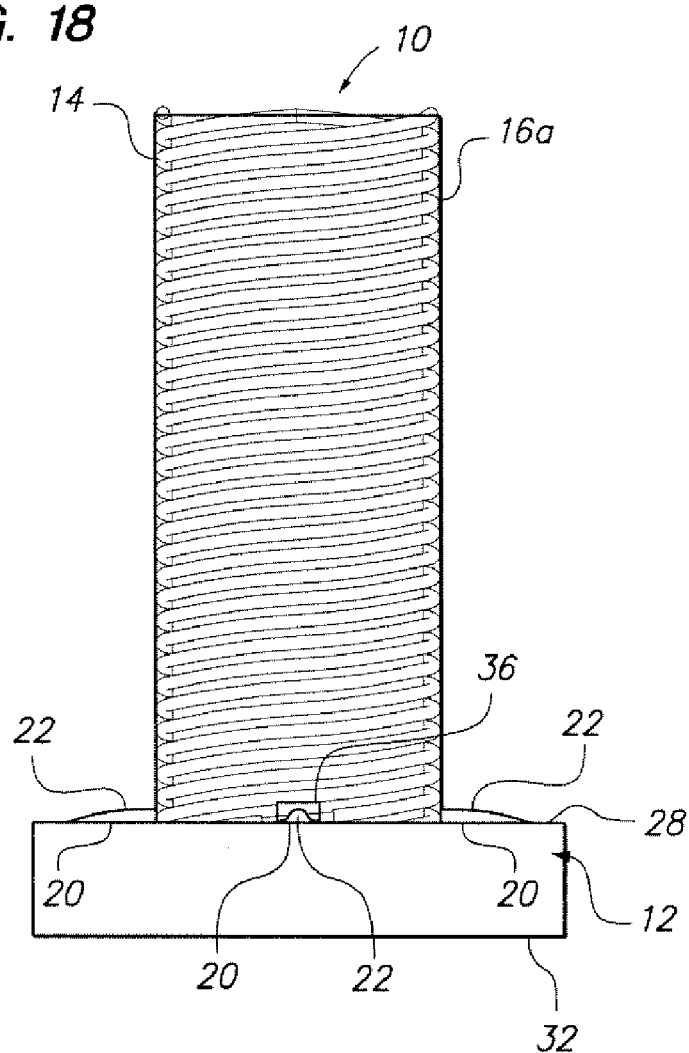
FIG. 18 is a side elevation view of a sixth example system.
Figure 19:
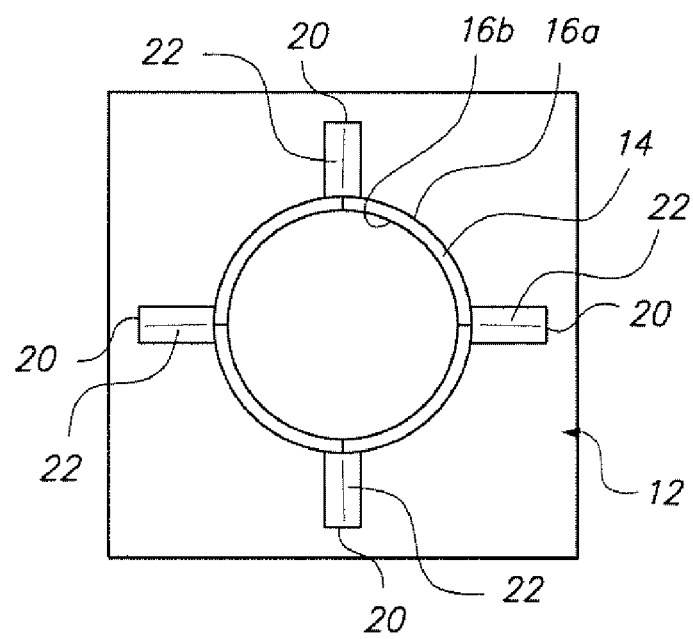
FIG. 19 is a top view of the example system of FIG. 18.

FIGS. 18 and 19 depict an alternative example of the system for electrically coupling a three-dimensional structure to a substantially two-dimensional structure. In this example, the dielectric substrate 12 does not have a through-hole 38, or holes positioned at the corners or anywhere else on the dielectric substrate 12. In this example, the coil of elements 10 terminates at the top surface 28 of the dielectric substrate 12. Thus, the wires 14 that are positioned at the end of the bundle of wires 14 of the coil of elements 10 terminate at the contact pads 20 established on the upper surface of the dielectric substrate 12. Similar to the previously described examples, the coil of elements 10 includes a plurality of wires 14 that are wound around an inner sheath 16b and constrained by an outer sheath 16a. The coil of elements 10 is cylindrical and the dielectric substrate 12 is shown as rectangular, however, any shapes for either of these elements may be utilized, if so desired. The outer sheath 16a includes a cutaway portion 36 where the wire 14 is coupled to the respective contact pad 20 utilizing connection solder 22. In the depicted examples in FIGS. 18 and 19, four contact pads 20 are utilized to couple to four wires that are disposed within the coil of elements 10. Each contact pad 20 is positioned on the dielectric substrate 12 such that it connects a different wire to each contact pad 20. The connection solder 22 may be coupled to each wire 14 via heating of the solder 22 such that it wicks onto the conductive portion of each wire 14 to establish an electrical and mechanical connection between the contact pad 20 and the wire 14.

It is possible to terminate the coils of wire 10 contained within the tubular structure at locations other than along the length of the tubular structure. FIGS. 18-19 illustrate just such a termination wherein the dielectric substrate 12 is disposed at an end of the tubular structure 10. End attached terminations can be combined with any and all of the above described termination methods.

Figure 20:
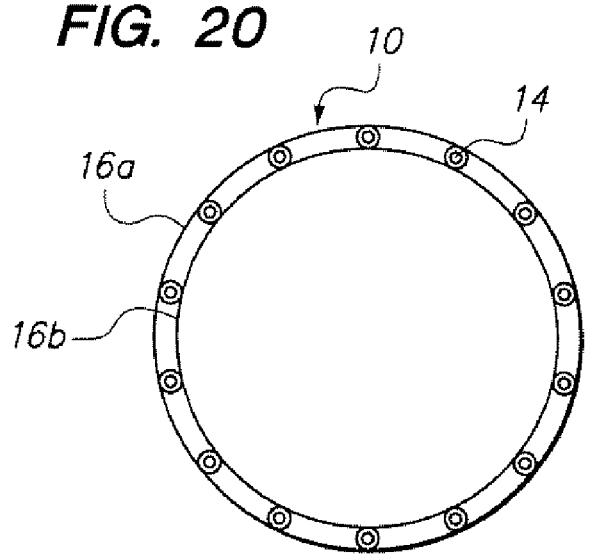
FIG. 20 is a cross-sectional view of an example coil of elements.

FIGS. 20-31 depict several different examples of a wire structure within a coil of elements 10. As shown in FIG. 20, a coil of elements 10 having a circular cross-section includes an inner sheath 16b and an outer sheath 16a. A plurality of wires 14 are disposed between the inner and outer sheaths 16b, 16a. FIG. 20 is similar to the examples previously disclosed. The wires 14 may be wound around the inner sheath 16b or the wires may be axially extending along the length of the coil of elements 10.

The tubular structure 10 need not have a round cross-section. FIGS. 20-31 demonstrate a representative subset of the possible cross sections of a tubular structure. Tubular structures 10 can have any number of different types of cross-sections such as round (FIGS. 20-22), oval (FIGS. 29-31), square (FIGS. 26-28), rectangular, pentagonal, triangular (FIGS. 23-25), or other shapes. Tubular structures 10 can also contain not just one central lumen, but a plurality of lumens of different sizes and configurations. What they all have in common is that a pattern of wires 14 exists around the tubular structure.

Figure 21:
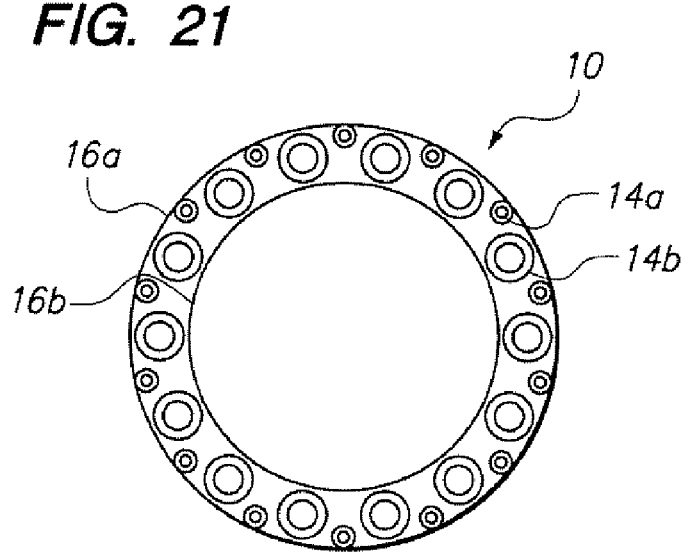
FIG. 21 is a cross-sectional view of a second example coil of elements.

FIG. 21 depicts a coil of elements 10 having a round cross-section, similar to that of FIG. 21, except for, in this example, two different sizes of wires 14 are provided. In this example, coil of elements 10 has an inner sheath 16b and an outer sheath 16a with a first-sized wire 14a evenly spaced around the circumference of the coil with an equal number of larger conduits 14b or wires positioned between each of the smaller conduits or wires 14a. In this example, the different shaped wires 14a, 14b may be used for different functions. For example, 14a is representative of a wire, while 14b is representative of a conduit or tube having a dissolvable center such that fluid can be transported through the center of the conduits 14b. Alternatively, wires could be positioned in either 14a and 14b and fluid could be positioned in 14a, if so desired. Although not previously discussed, the present system may be utilized to establish both electrical connections and fluid connections. In each of the previously disclosed examples, the wires could alternatively be channels, tubes, or other conduits for transporting a fluidic material including liquids, gases, or other such materials. In the case where fluid is transported through the wires 14, the dielectric substrate 12 would have an associated conduit channel or other feature for receiving the fluid in a fluid type manner. This will be discussed in greater detail below. However, as shown in FIG. 21, it is possible to have both fluid transporting conduits and wires within the coil of elements 10.

Figure 22:
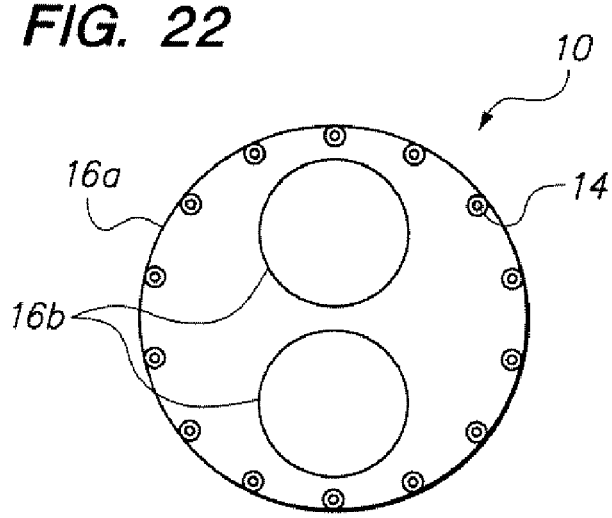
FIG. 22 is a cross-sectional view of a third example coil of elements.

FIG. 22 depicts an alternative example where an outer sheath 16a is provided with two inner sheaths 16b. The inner sheaths 16b define openings within the coil of elements 10 that extend axially along the length of the coil of elements 10. In the depicted example of FIG. 22, the inner sheaths define two cylindrical openings that extend axially within the coil of elements 10. Wires 14a may be positioned around the periphery of the coil of elements 10 adjacent the outer sheath 16a.

Figure 23:
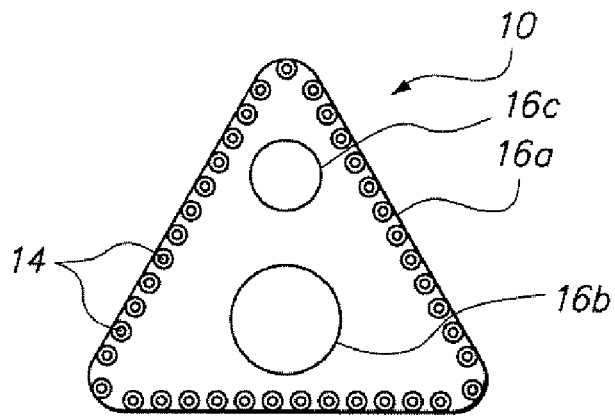
FIG. 23 is a cross-sectional view of a fourth example coil of elements.
Figure 24:
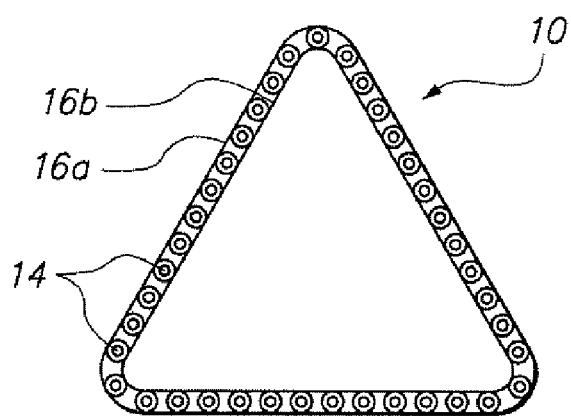
FIG. 24 is a cross-sectional view of a fifth example coil of elements.
Figure 25:
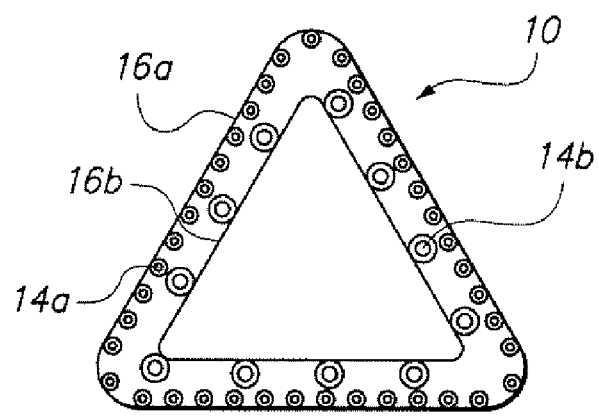
FIG. 25 is a cross-sectional view of a sixth example coil of elements.

FIGS. 23-25 depict alternative examples similar to those previously discussed, except that in this case the coil of elements 10 is triangular in shape. The coil of elements 10 is bounded on the outside by sheath 16a and on the inside by sheaths 16b and 16c. The plurality of wires 14a or conduits 14b are disposed around the periphery of the coil of elements 10, and the wires 14 may be either wound around the coil of elements 10 or disposed axially along the length of the coil of elements 10.

FIG. 24 depicts a triangular coil of elements 10 having an inner sheath 16b and an outer sheath 16a with a plurality of wires 14 disposed between the inner and outer sheaths. In this example, the wires 14 are evenly distributed around the periphery of the coil of elements 10. As with prior examples, the wires 14 may be wound around the circumference of the inner sheath 16b or the wires 14 may extend axially along the length of the coil of elements 10.

FIG. 25 depicts a similar triangular coil of elements 10 having an inner sheath 16b and an outer sheath 16a. A plurality of wires are disposed around the coil of elements 10. A smaller wire 14a is disposed around an outermost periphery of the coil of elements 10 and an inner larger wire 14b is equally spaced around the inner sheath 16b. There are more wires 14a than wires 14b. Although this example is discussed in the context of wires within the coil of elements 10, it should be recognized that the elements 14a and 14b could be either wires or conduits or passageways for receiving a fluid, such as liquids or gases.

Figure 26:
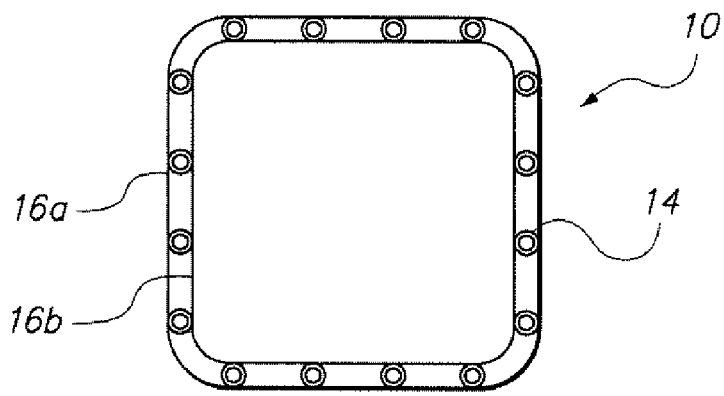
FIG. 26 is a cross-sectional view of a seventh example coil of elements.
Figure 27:
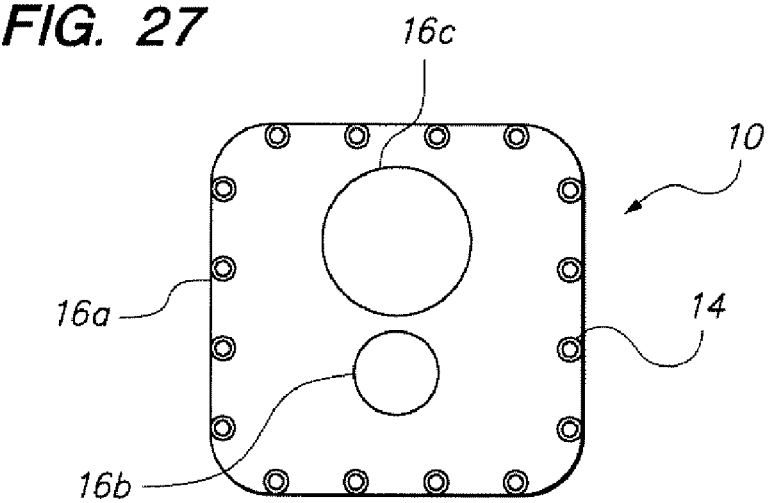
FIG. 27 is a cross-sectional view of an eighth example coil of elements.
Figure 28:
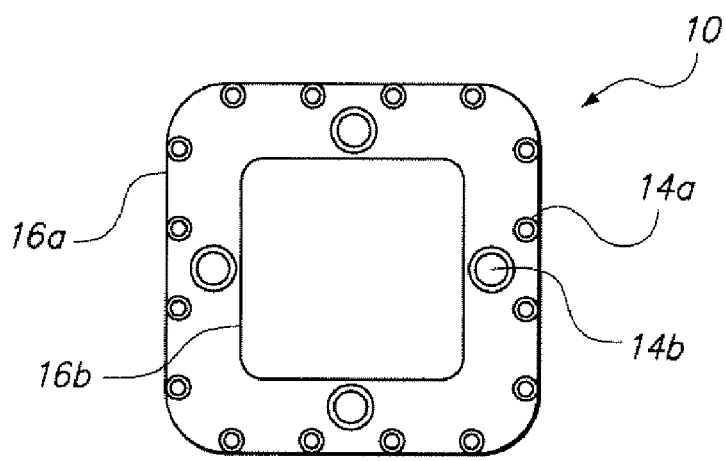
FIG. 28 is a cross-sectional view of a ninth example coil of elements.

FIGS. 26-28 depict an alternative example of the coil of elements 10 where the outer periphery of the coil of elements 10 is substantially rectangular. In the depicted examples in FIGS. 26-28, the coil of elements 10 is a square shape. FIG. 26 includes an outer sheath 16a and an inner sheath 16b. A plurality of wires 14 are equally spaced around the periphery of the coil of elements 10 between the inner and outer sheaths 16a, 16b.

FIG. 26 depicts a square outer sheath 16a. Two inner sheaths 16b, 16c are defined as circular tubes or cylinders that extend through the interior of the coil of elements 10. One of the inner sheaths 16c has a larger diameter than the other inner sheath 16b. A plurality of wires 14 are disposed inside the outer sheath 16a and evenly spaced around the periphery of the coil of elements 10.

FIG. 28 depicts a coil of elements 10 having an outer sheath 16a that is square in shape and an inner sheath 16b that is a similar square shape. A plurality of wires 14a, 14b are positioned between the inner and outer sheaths. The wires include smaller diameter wires 14a that are positioned nearest to the outer sheath 16a and a plurality of inner larger diameter wires 14b that are spaced around the inner sheath 16b. The inner wires 14b are fewer in number than the outer wires 14a, and each of the wires are evenly spaced around the periphery of the coil of elements 10.

As previously discussed in connection with prior examples, the elements described as wires 14, 14a and 14b in FIGS. 26-28 could alternatively be conduits or passageways for transporting a fluid such as a gas or a liquid. The examples are not to be limited to simply wires having electrical connectors disposed therethrough. The wires 14 could alternatively be plastic coated tubes having a dissolvable material inside the tubes such that when the dissolvable material is dissolved, a conduit for a fluid is provided.

Figure 29:
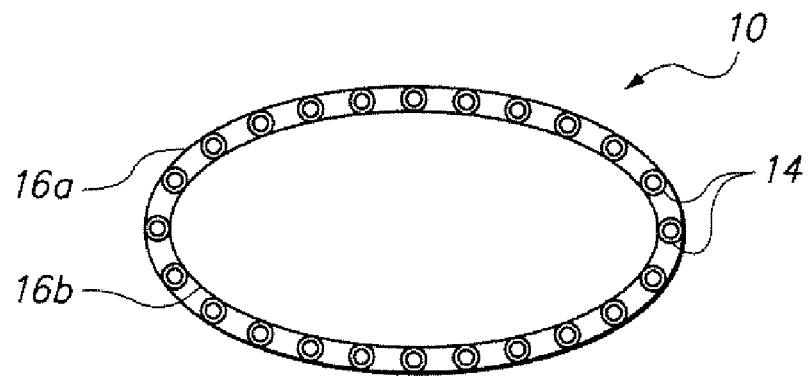
FIG. 29 is a cross-sectional view of a tenth example coil of elements.
Figure 30:
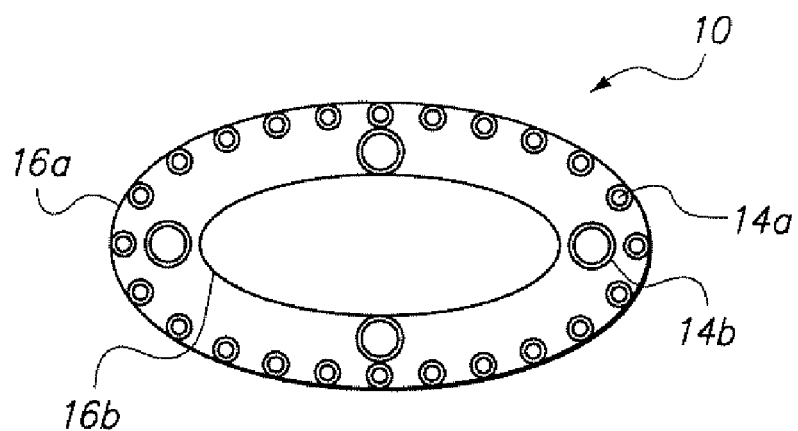
FIG. 30 is a cross-sectional view of an eleventh example coil of elements.
Figure 31:
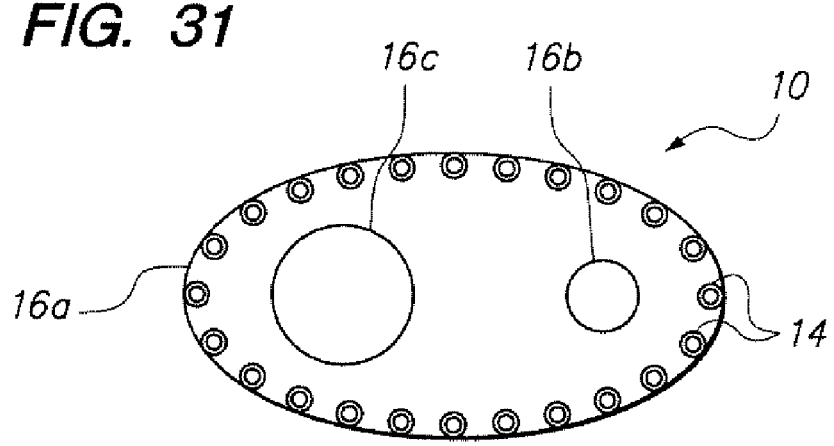
FIG. 31 is a cross-sectional view of a twelfth example coil of elements.

FIGS. 29-31 depict an alternative example of a coil of elements 10 similar in many respects to the examples previously discussed. Each of the examples in FIGS. 29-31 has an oval shaped outer periphery. FIG. 29 includes an inner sheath 16b and an outer sheath 16a which together bound an interior space having a plurality of wires 14 disposed therein. The plurality of wires 14 are evenly spaced around the periphery around the coil of elements 10. The wires 14 may be wound around the inner sheath 16b or may be axially extending along the length of the coil of elements 10.

FIG. 30 depicts an inner sheath 16b and an outer sheath 16a with a plurality of wires 14a, 14b disposed between the inner and outer peripheries and evenly spaced around the periphery thereof. In this example, two different sized wires 14a, 14b are provided. A smaller diameter wire 14a is evenly spaced around the outer periphery of the coil of elements 10 adjacent the outer sheath 16a. An inner plurality of wires 14b, having a larger diameter than the outer wires 14a, are disposed adjacent the inner sheath 16b. The smaller wires 14a are far more numerous than the larger wires 14b in this example coil of elements 10. FIG. 31 discloses an outer sheath 16a and two inner sheaths 16b, 16c. A plurality of wires 14 are disposed between the inner and outer sheaths 16b, 16a, 16c.

The inner sheaths 16b, 16c form cylinders having a circular cross-section that extend axially along the length of the coil of elements 10. One of the inner sheaths 16c forms a larger diameter circle than the other inner sheath 16b, which forms a smaller diameter circle than the larger diameter circle. The plurality of wires 14 are disposed around the outer edge of the coil of elements 10 adjacent the outer sheath 16a. In this example, only one diameter wire is disclosed, however, it should be recognized in any of these examples, that any number of wires and any size wires may be utilized to the extent that they fit within the area between the inner and outer sheaths 16a, 16b, 16c. Also, as previously discussed, while the above description was in the context of wires 14, which typically will have a conductive material positioned within an outer plastic coating, the wires may alternatively be tubes for transporting a fluid such as a gas or a liquid.

Figure 32:
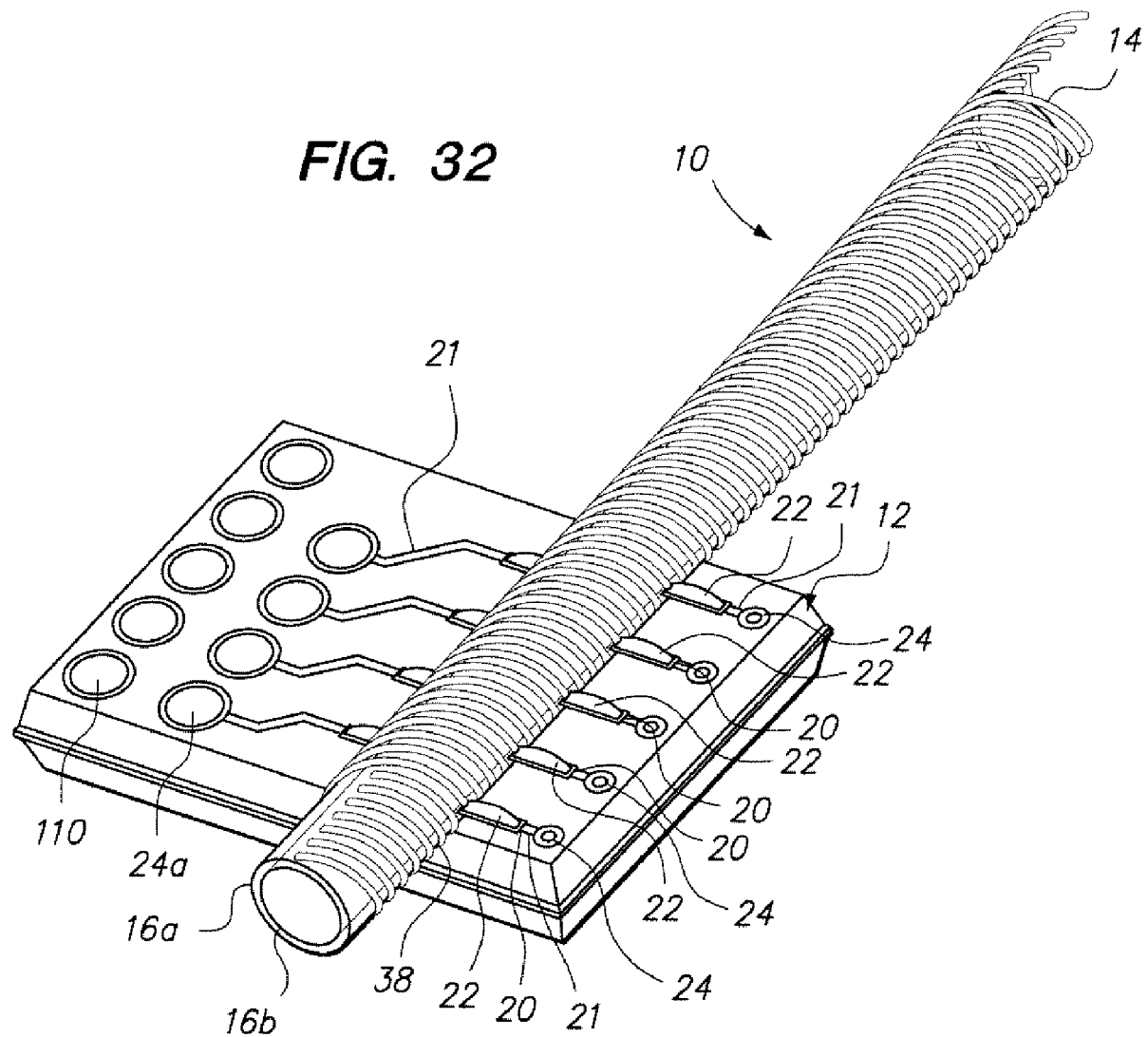
FIG. 32 is a perspective view of a seventh example system.

FIG. 32 depicts an alternative example of the system for electrically coupling a three-dimensional structure to a substantially two-dimensional structure. In this example, a coil of elements 10 is disposed within a recess or passageway 38 that is defined in the surface 28 of substrate 12. While prior examples positioned the coil of elements 10 perpendicular to the dielectric substrate 12, in this example, the axis of the coil of elements 10 is substantially perpendicular to the surface 28 of the dielectric substrate 12. A recess 38 is defined within the upper surface 28 of the dielectric substrate 12 in order to receive at least a portion of the coil of elements 10 therein. The coil of elements 10 is depicted as seating in the recess 38 such that part of the coil of elements 10 is positioned below the surface 28 of the dielectric substrate 12 and part of the coil of elements 10 as positioned above the surface of the dielectric substrate 12. It will be recognized that any shape of opening or recess in the dielectric substrate 12 could be utilized such that the coil of elements 10 is positioned at different depth levels within the dielectric substrate 12. The position of the coil of elements 10 relative to the dielectric substrate 12 is, in part, dependent upon the thickness of the dielectric substrate 12.

The coil of elements 10 includes an inner sheath 16b and an outer sheath 16a, with the inner sheath 16b serving as a boundary for a spirally wound plurality of wires 14 that are positioned between the inner and outer sheaths 16b, 16a. The wires 14 of the coil of elements 10 are coupled to contact pads 20 having solder 22 disposed thereon in a manner similar to that previously discussed in connection with the prior examples. The only difference is that the coil of elements 10 is positioned on its side instead of being straight up and down. In this example, the outer sheath is cut to expose the wires 14 inside the coil of elements 10 and each respective wire 14 that is to be coupled to a contact pad 20 is also stripped of its protective outer coating 26 in order to reveal the underlying conductive material 40 within the wire 14. As previously discussed, in connection with the prior examples, solder 22 positioned on the contact pad 20, upon heating, couples to the conductive material 40 within each wire 14 that is aligned for coupling.

The dielectric substrate 12 in this example shows electrical traces 103 that extend from the contact pads 20 to other components. The example shown in FIG. 32 also incorporates a heat transfer pad 24 that is conductively coupled to the contact pads 20. The heat transfer pad 24 is designed to accept heat from a heating element, to transfer the heat to the contact pad 20 which then melts the solder 22 that is positioned on the contact pad 20, such that the solder 22 wicks or couples to an adjoining wire 14 within the coil of elements 10. The heating pad 24 may be spaced from the contact pad 20 by a conductive conduit 21 which is essentially a pad of conductive material that is coupled to the heat transfer pad 24 and to the contact pad 20. A secondary dielectric (not shown) may be positioned over the conductive conduit 21 such that communication between the heating pad 24 and the contact pad 20 is avoided. The heating pad 24 is also a conductive element that is positioned on a surface of the dielectric substrate 12. Alternatively, the elements referred to as "heating pads" may be connector holes 24 for receiving a connector for coupling to the wire 14. The holes 110 on the left side of the dielectric substrate 12 may be utilized for positioning connectors therein or for coupling to a pin or other similar connector.

Figure 33:
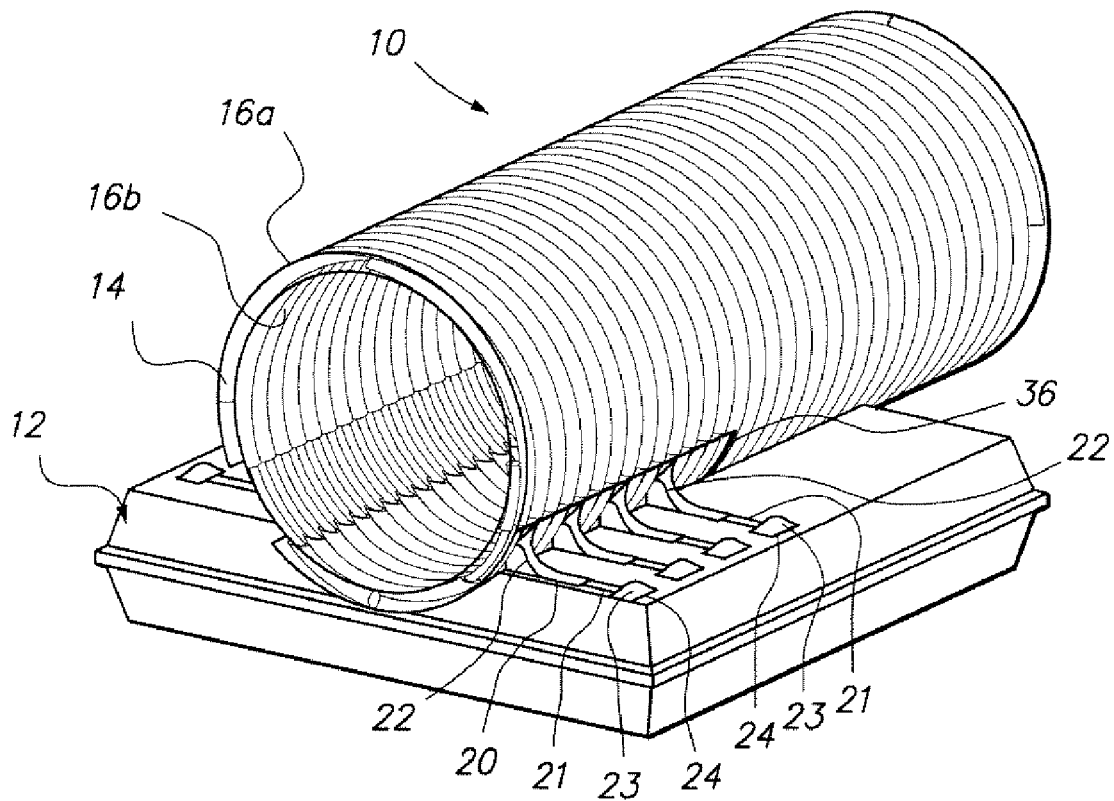
FIG. 33 is an expanded perspective view of the example system, similar to that of FIG. 32.

FIG. 33 is a expanded view of the connection between the wires 14 and the contact pad 20 of the example shown in FIG. 32. In this figure, the outer sheath 16a of the coil of elements 10 is cut away in the vicinity of the wires 14 to be coupled to the contact pads 20 disposed on the dielectric substrate 12. The protective coating of the wires 14 may be fully stripped in the vicinity of the opening 36 in the outer sheath 16a, in order to allow the wires 14 to be coupled to the connection solder 22. As with prior examples, the wires 14 may be joined to the connection solder 22.

In FIG. 33, the longitudinal axis of the coil elements 10 is substantially perpendicular to the upper surface 28 of the dielectric substrate 12. Depending upon the thickness of the dielectric substrate 12 and the diameter of the coil of elements 10, the longitudinal axis of the coil of elements 10 could align with the upper surface 28 of the substrate 12 or be positioned above or below the upper surface 28 of the substrate 12. The solder connection for FIG. 33 includes a contact pad 20 having a solder 22 disposed thereon. A heat transfer pad 24 of conductive material is coupled to the contact pad 20 by a conductive conduit 21. The heat transfer pad 24 has disposed thereon a heat transfer material 23 such that when the heat transfer material 23 of the heat transfer pad 24 comes in contact with a heat source, the heat is transmitted from the heat transfer pad 24 through the conductive conduit 21 to the contact pad 20 which then heats the solder 22 disposed on the contact pad 20. The solder 22 then wicks onto the exposed wire 40 in the vicinity of the solder 22 to establish an electrical and mechanical connection between the contact pad 20 and the wire 14.

Figure 34:
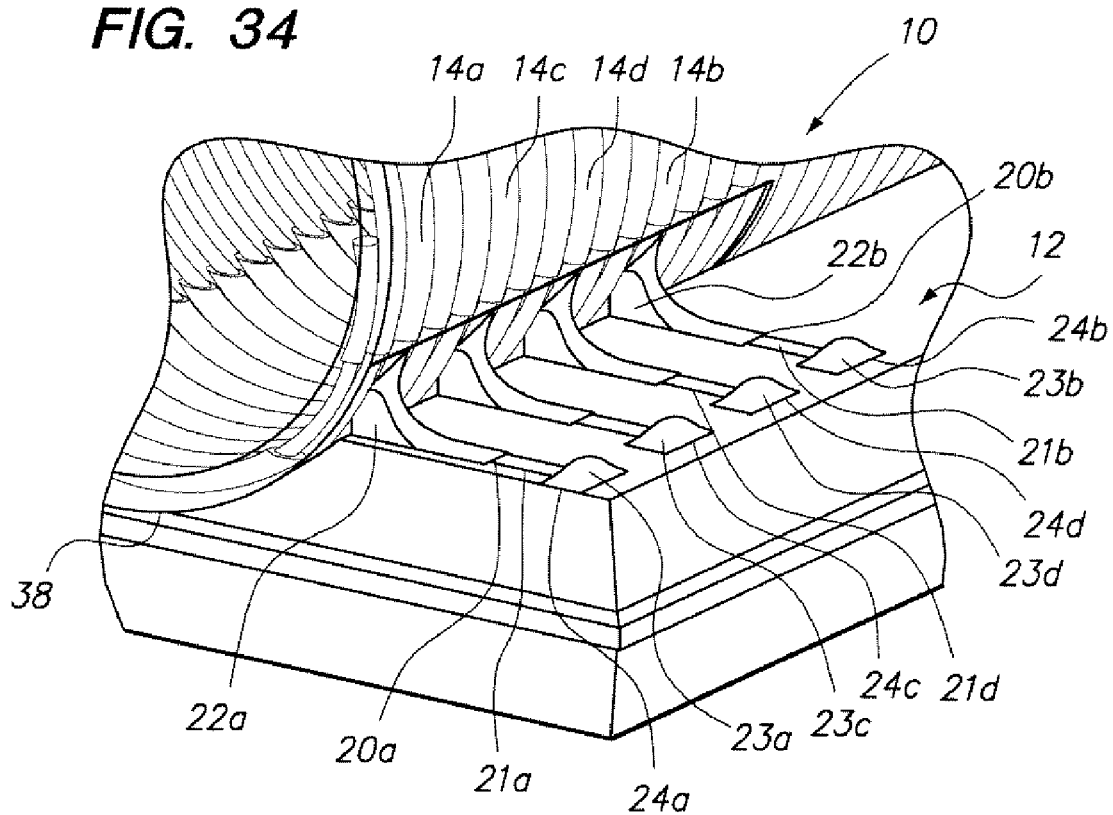
FIG. 34 is a more closely expanded perspective view of the system of FIG. 32.

FIG. 34 depicts an example of how wires 14 are numbered within a coil of wires 10. In this example, a first wire 14a is coupled to the first contact pad 20a, a second wire 14b is coupled to the last contact pad 20b, a third wire 14c is coupled to the third contact pad 20c, and a fourth wire 14d is coupled to the fourth contact pad 20d. A similar set of contact pads is disposed on the left side of the coil of elements 10. Depending upon the pitch of the wires 14 in the coil of elements 10, the wires 1 through 4 will be arranged in a similar scheme on the left side of the coil of elements 10, or a different arrangement. For example, the wire connections on the left side of the coil of elements 10 on the dielectric substrate 12 could be arranged in numerical order starting with 1 through 4. Or, the numbers could be switched around depending upon the pitch of the windings of the wires 14 in the coil of elements 10.

FIG. 34 illustrates a method of soldering a substantially three dimensional structure to a substantially two dimensional structure. Specifically, a three dimensional coil 10 of wound wire or wires 14a-14d is attached to a substrate 12 with the use of a connection material 22 displaced on a connection pad 20 which has been permanently affixed to the substrate 12 and can be easily defined in terms of length and width. In addition, a heat transfer pad 24a-24d, having heat transfer material 23a-23d, is coupled to contact pad 20a-20d via a conductive conduit 21a-21d. The coil 10 can be used in a medical device such as a probe that is inserted into the human body, but the current invention is not so limited. The coil 10 need not have a constant cross section for its entire length, indeed the coil can expand and contract at predetermined points along its length independent of the tubular structure. The coil 10 can surround a hollow tube, solid tube, guide wire, optical fiber, cavity, etc. All of these structures are hereafter referred to as a tubular structure 16 which will be discussed in detail below. In general, a tubular structure contains an outer surface 16a and an inner surface 16b and the wires 14 are contained within the tubular structure 16.

Figure 35:
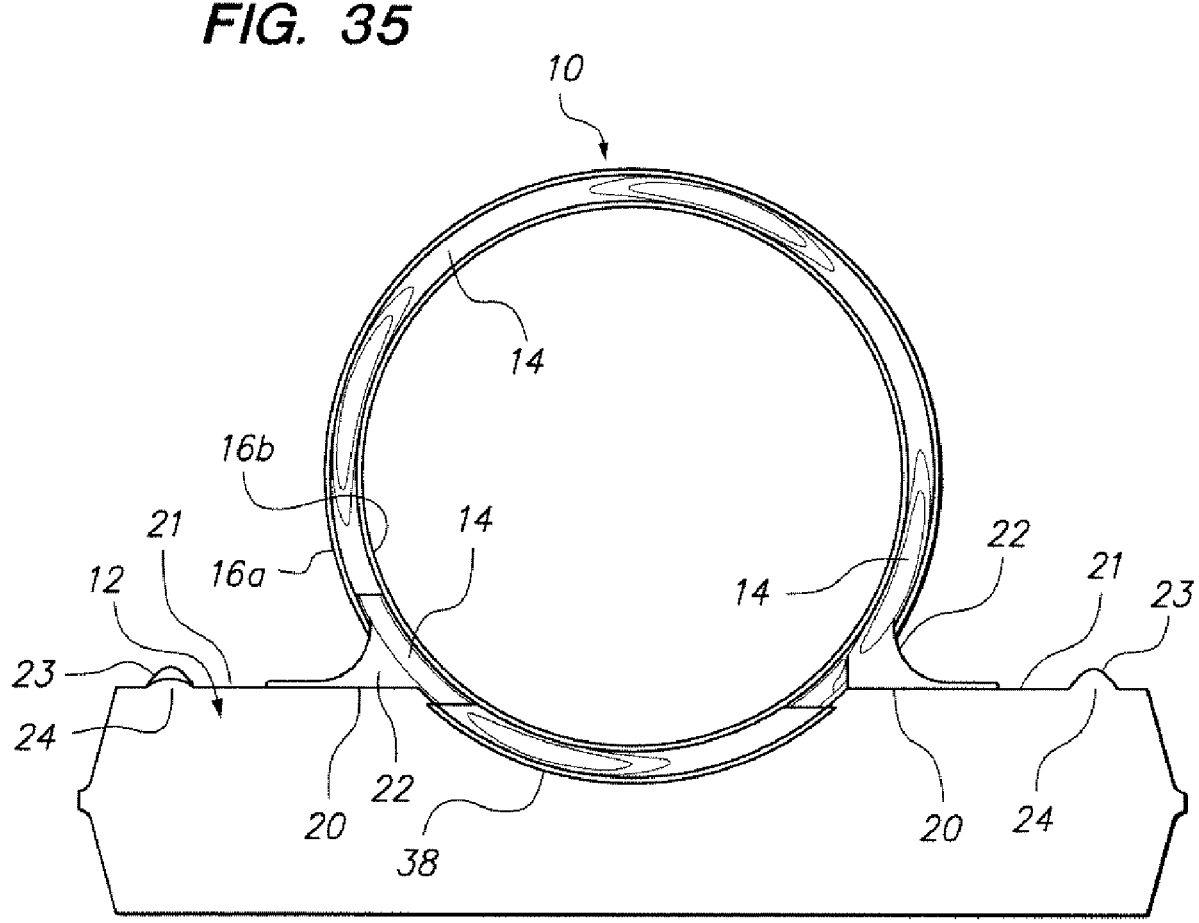
FIG. 35 is a cross-sectional view of the system of FIG. 33.

FIG. 35 shows a cross section of the coil 10, the wires 14, the substrate 12, as well as connection material 22, conductive conduit 21, connection pads 20, heat transfer pads 24, and heat transfer material 23, along a common, arbitrary plane. During the wetting of the wire 14 by the connection material 22, the connection material 22 wraps around the wire 14 forming a good mechanical joint at the interface of the groove 18 and the connection pad 20.

Figure 36:
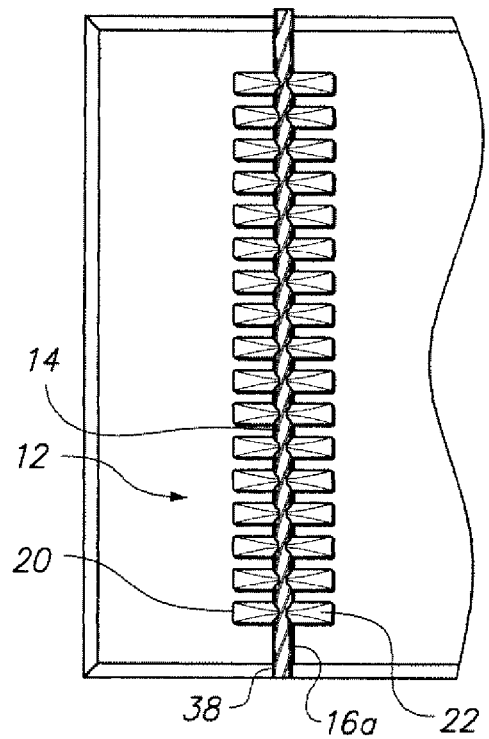
FIG. 36 is a top view of an eighth example system.
Figure 37:
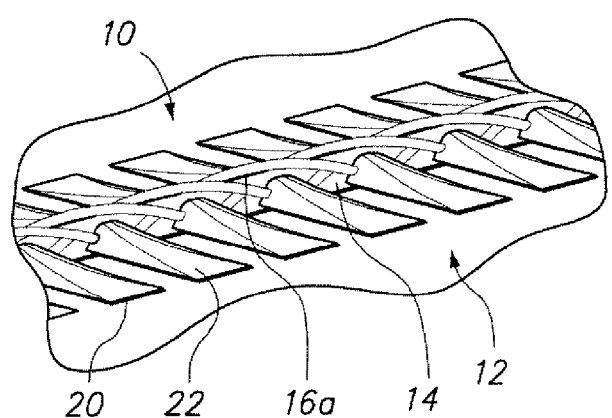
FIG. 37 is an expanded, perspective view of the example system of FIG. 36.
Figure 38:
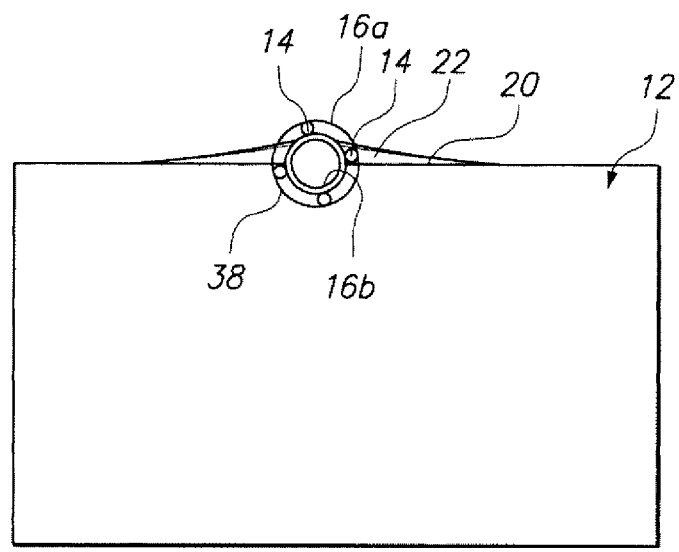
FIG. 38 is a cross-sectional view of the example system of FIG. 36.

FIGS. 36, 37 and 38 illustrate another way to attach a substantially three dimensional structure to a substantially two dimensional substrate 12. Each wire 14 is wound around a tubular structure 16 that is placed within a groove 38 of a substrate 12. Connection pads 20 are disposed along a planar surface of the substrate 12 at the spacing of the wires 14. Specifically, when tubular structure 16 is laid in the groove 38, each wire 14 intersects the substrate 12 at multiple locations. Contact pads 20 are applied to the substrate 12 at those locations where the wires 14 intersect the substrate 12 and connection material 22 is applied to the top surface of all the connection pads 20.

Figure 39:
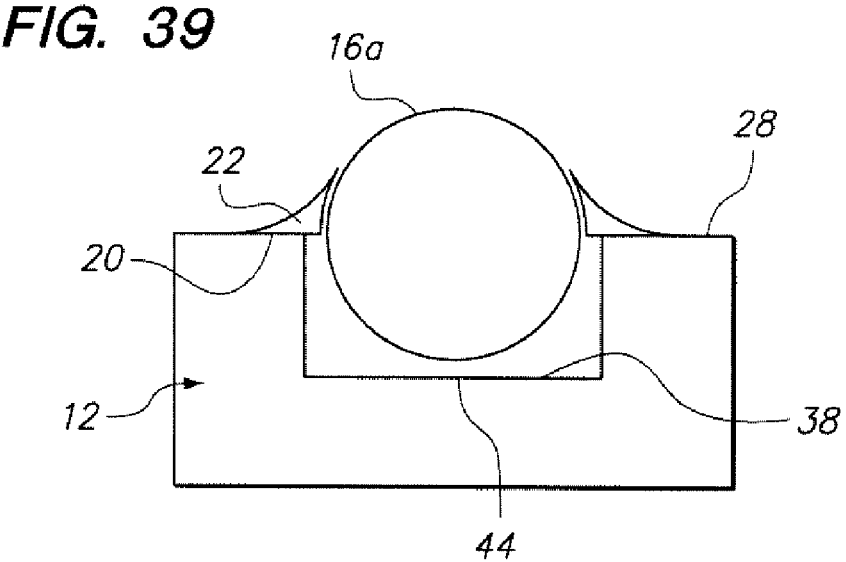
FIG. 39 is a cross-sectional view of a ninth example system.

FIGS. 39 through 44 depict alternative examples of the connection between the coil of elements 10 and the opening 38 disposed in the dielectric substrate 12. In FIG. 39, the channel that is positioned in the top surface 28 of the dielectric substrate 12 for receiving the coil of elements 10 has a rectangular cross-section. As shown, a side of the coil of elements 10 is positioned at the bottom 44 of the rectangular recess 38. In this example, the longitudinal axis of the coil of elements 10 is substantially aligned with the surface 28 of the dielectric substrate 12. Connection solder 22 is utilized to connect wires 14 within the coil of elements 10 to respective contact pads 20 on the surface 28 of the dielectric substrate 12.

Figure 40:
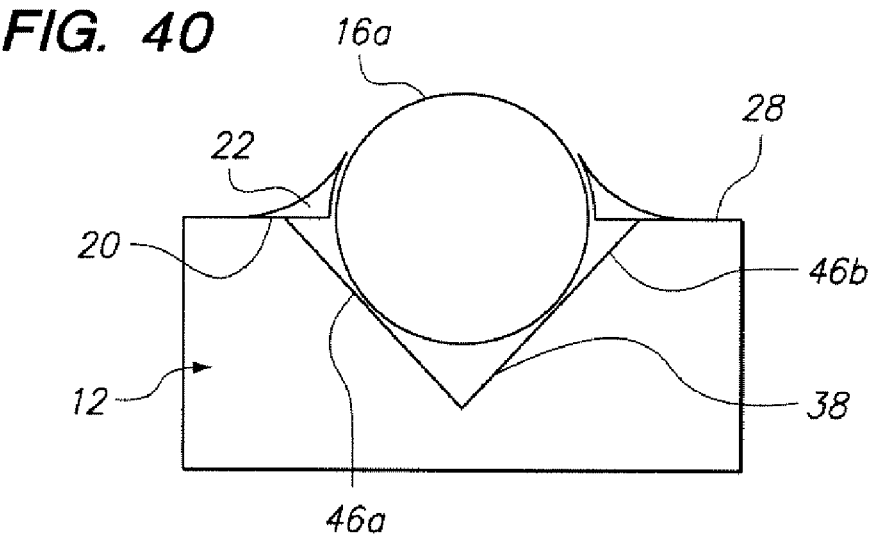
FIG. 40 is a cross-sectional view of a tenth example system.

FIG. 40 depicts an alternative example of a recess 38 in the surface of the dielectric substrate 12 that is V-shaped such that two sides of the coil of elements 10 rests upon the two sides 46a, 46b of the V-shaped channel 38. Connection solder 22 is utilized to couple wires 14 disposed within the coil of elements 10 to contact pads 20 that are disposed on the surface 28 of the dielectric substrate 12. As with FIG. 39, the longitudinal axis of the coil of elements 10 is substantially aligned with the surface 28 of the dielectric substrate 12.

Figure 41:
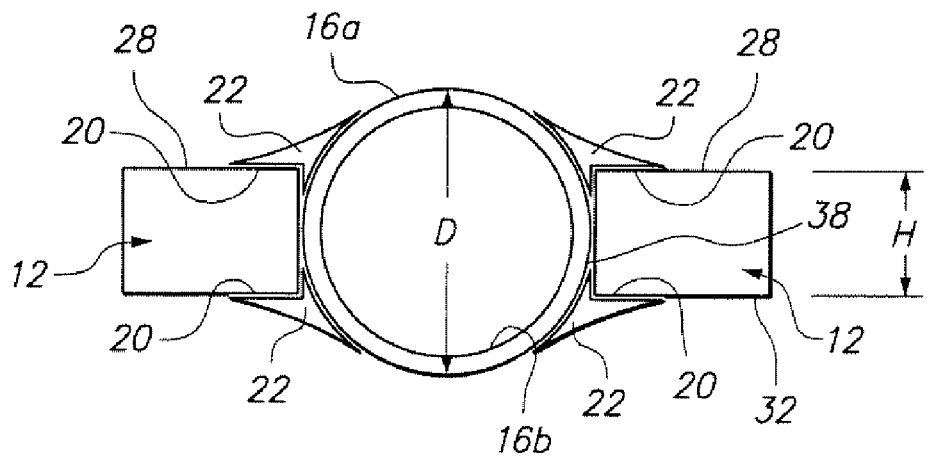
FIG. 41 is a cross-sectional view of an eleventh example system.

FIG. 41 depicts a coil of elements 10 positioned between two dielectric substrates 12. A horizontal axis of the dielectric substrates 12 aligns with the longitudinal axis of the coil of elements 10. The dielectric substrates 12 have a height H that is less than the diameter D of the coil of elements 10. As such, when the coil of elements 10 is positioned between the dielectric substrates 12, a portion of the coil of elements 10 extends above the top surfaces 28 of the dielectric substrates 12 and a portion of the coil of elements 10 extends below the bottom surfaces 32 of the dielectric substrates 12. Connection solder 22 is utilized on both the top and bottom surfaces 28, 32 of the dielectric substrates 12 to couple the conductive wires 14 of the coil of elements 10 to the contact pads 20 that are disposed on the surfaces 28, 32 of the dielectric substrates 12.

Figure 42:
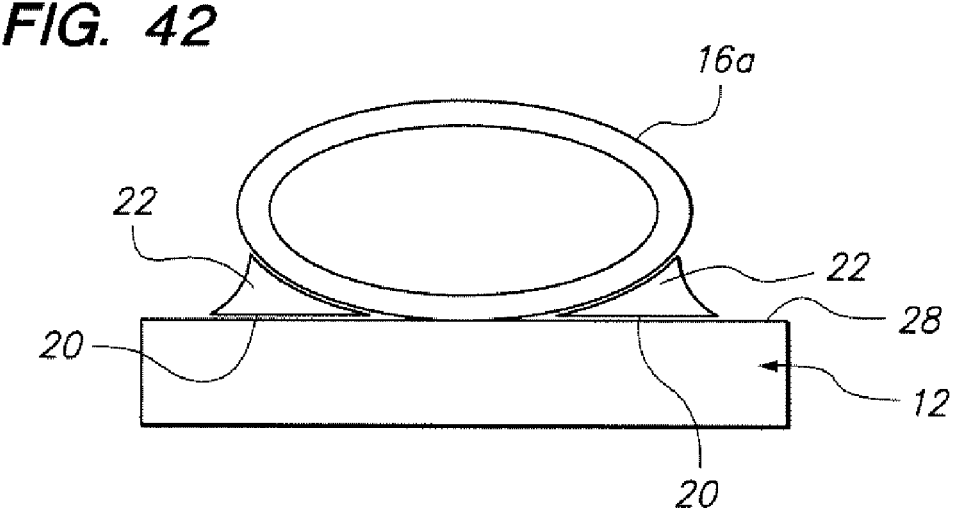
FIG. 42 is a cross-sectional view of a twelfth example system.
Figure 43:
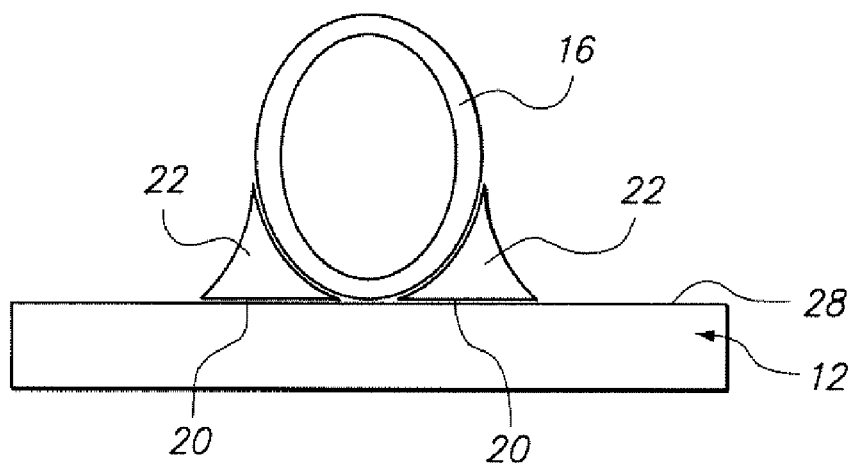
FIG. 43 is a cross-sectional view of a thirteenth example system.
Figure 44:
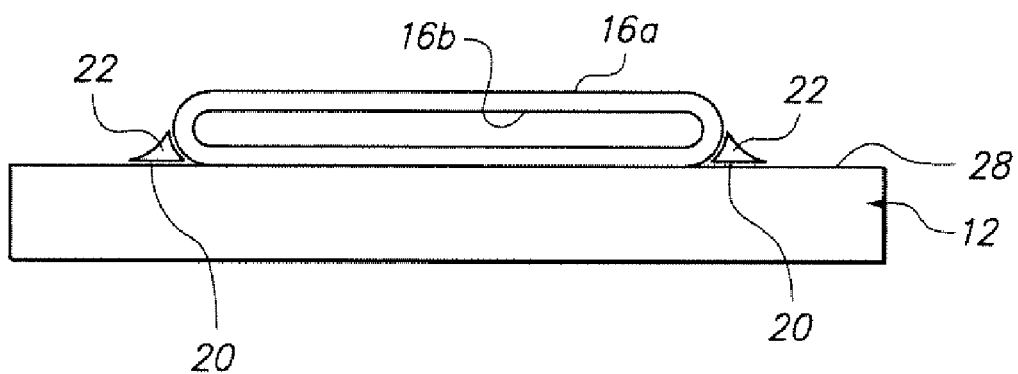
FIG. 44 is a cross-sectional view of a fourteenth example system.

FIGS. 42 through 44 depict a coil of elements 10 that is positioned on the top surface 28 of the dielectric substrate 12. In these examples, a recess for retaining the coil of elements 10 is created by the connection solder 22 that is utilized to connect the contact pads 20 to the conductive elements or wires 14 within the coil of elements 10. No recess 38 is defined in the surface 28 of the dielectric substrates 12.

FIG. 42 depicts an oval coil of elements 10 wherein the long transverse axis of the oval is positioned parallel to the surface 28 of the dielectric substrate 12. The connection solder 22 is positioned substantially under the edges of the coil of elements 10.

FIG. 43 depicts an oval-shaped coil of elements 10 where the long transverse axis of the oval shape is positioned perpendicular to the surface 28 of the dielectric substrate 12. The oval shape is held on the dielectric substrate 12 by the connection solder 22, which forms supports for the coil of elements 10. The connection solder 22 is positioned on the contact pads 20 and a portion of the connection solder 22 is positioned under the edges of the coil of elements 10 and a portion of the connection solder 22 extends outwardly from the edges of the coil of elements 10.

FIG. 44 depicts a coil of elements 10 having a cross-sectional shape like that of a racetrack. A long transverse axis of the coil of elements 10 is disposed parallel to the surface 28 of the dielectric substrate 12. Connection solder 22 is positioned on the contact pads 20 and is coupled to the wires 14 of the coil of elements 10 in order to establish an electrical and mechanical connection between the wires 14 and the contact pad 20. The connection solder 22 supports the coil of elements 10 on the surface of the dielectric substrate 12.

FIGS. 32-44 show how it is not necessary for the tubular structure and the dielectric to be arranged perpendicularly to one another by using a channel or a groove that has been formed into the surface of a dielectric substrate 12, the tubular structure can be mechanically retained by attachment to connection pads 20. With the correct profile of a tubular structure, a channel 38 on a dielectric substrate 12 is not even required. Instead, the tubular structure can have a flat side which rests flush with the dielectric substrate (such as shown in FIG. 44).

FIGS. 45 through 49 depict different examples of tubular structures that contain coils of wire 10. The wires 14 in the examples can be moving in opposite directions, such as clockwise and counterclockwise. The alternating coils form braided or woven structures along the length of the tubular structure 10.

Figure 45:
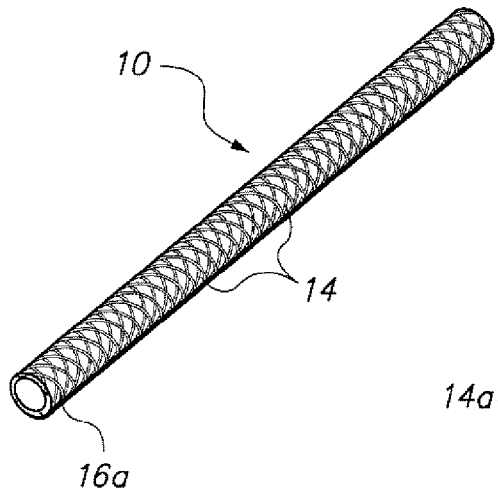
FIG. 45 is a cross-sectional view of an example coil of elements for use in the system.
Figure 46:
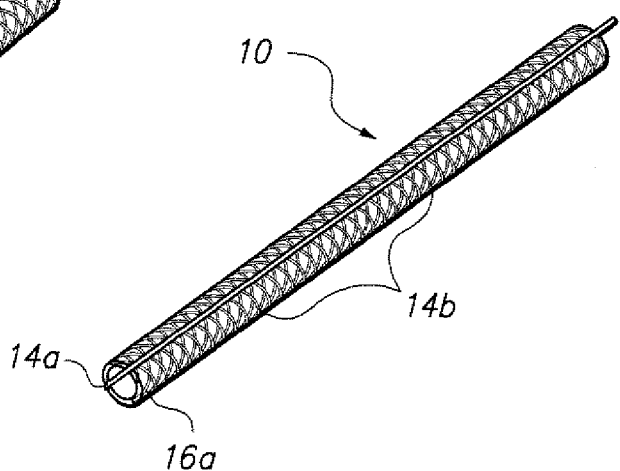
FIG. 46 is a cross-sectional view of a second example coil of elements for use in the system.
Figure 47:
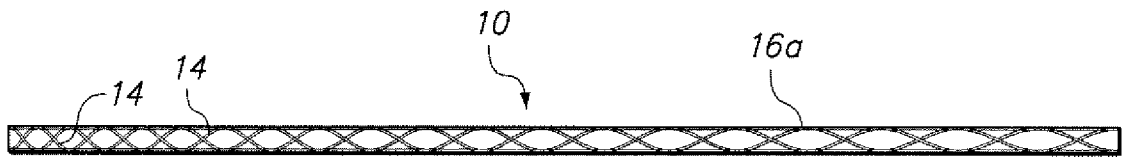
FIG. 47 is a transparent side elevation view of a third example coil of elements for use in the system.
Figure 48:
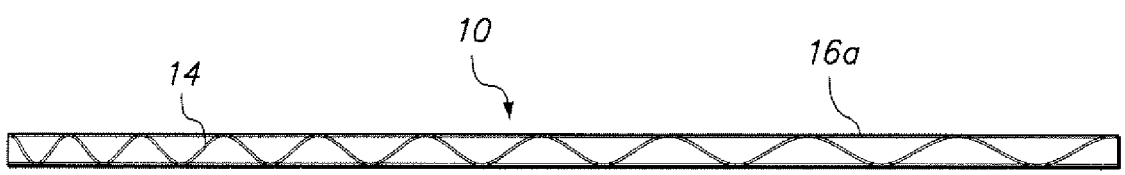
FIG. 48 is a transparent side elevation view of a fourth example coil of elements for use in the system.
Figure 49:
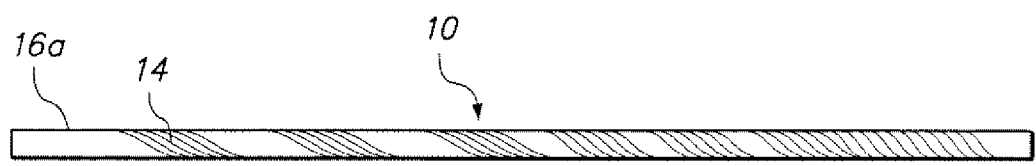
FIG. 49 is a side elevation view of a fifth example coil of elements for use in the system.

FIG. 45 shows an example where the wires 14 are braided on the surface of the tubular structure 16a with one wire going in a first direction and the other wire going in a second direction. FIG. 46 is similar to FIG. 45, but includes a wire 14a that extends longitudinally along the length of the tubular structure 10. FIG. 47 depicts two wires disposed around the surface 16a of a tubular structure 10, with the windings of the wires 14 having different pitches depending upon the location of the wires 14 along the length of the tubular structure 10. FIG. 48 is similar to FIG. 47 except for it only includes a single wire traveling in a single direction. The wire has a different pitch at the one end than at the other end. FIG. 49 represents a winding of wires around the tubular structure. The windings have a different pitch at one end and at the other, the pitch gradually changes between the one end and the other end.

FIGS. 45-49 show how the coil of wire can be combined with other structures inside or alongside the tubular structure. The coil can contain wires 14 moving in opposing directions, i.e. clockwise and counterclockwise turns. These alternating coils can interact with each other and form woven or braided structures along the length of the tubular structure 10. Not all of the individual wires 14 contained within such a braided structure need to be electrically conductive or attached to a dielectric substrate 12. Selective stripping of the insulation 26 allows for precise control over what is attached to what. Indeed, straight runs of wire (not shown) can be combined with either the braided structure or with regular coils of wire. These straight runs can be for either selective impedance matching, electrical attachment, or as non-conductive safety wires. It is also not necessary for all the wire strands 14 in a coil 10 to be of the same size or of the same material. For example, thermocouple pairs can be run down within the coil of wire 10 and mixed gauge wires can be used to both further refine the flexibility characteristics of the tubular structure and to enhance the electrical communication of the system.

FIGS. 50-55 represent a fluidic structure that is configured to accept fluids, gases or semi-fluid or particulate matter transfer. The term conductive element as used herein in connection with the coil of wires 10 is defined to include both electrical transmission and fluidic transmission of an element, such as a fluid, a gas, a cryogen, a particulate, and a semi-solid. As previously discussed, the wires 14 may alternatively be tubes that are filled with a dissolvable material such that when the material inside the tube is dissolved, a hollow member 14 for transporting the fluid is provided. In order to connect such a hollow member 14 containing a dissolvable material to a substrate 12, the covering 112 of the dissolvable material within the tube may be stripped at a location where the tube is to be connected with a substrate, such as a dielectric substrate 12 depicted in FIG. 50. Alternatively, the tube can be positioned adjacent a channel opening 106 in a substrate 12 without stripping.

Once the protective material 112 around the dissolvable material is stripped away, leaving the dissolvable material, an epoxy or other plastic type of sealing material 114 may be positioned over the dissolvable material to define a conduit 107 through which a fluid can flow once the dissolvable material has been dissolved. As shown in FIGS. 50-55, a channel 106 is disposed in a substrate 12 and the tube 14 is in communication with that conduit 106. A temporary gusset 105 is disposed adjacent the tube of dissolvable material and is utilized to hold the tube in place and to seal around the tube to create the channel from the tube to the channel that is defined within the substrate 12. The tube filled with dissolvable material is coupled to the channels 106 that is defined in the substrate 12. In addition, the example coil of elements 10 can include both a conductive wires and tubes filled with dissolvable material. Gusset 105 can be an epoxy-type sealing material, or other material that can be used to seal the tube of dissolvable material to a corresponding conduit in the substrate 12. The electrical connections and fluidic connection can be used side-by-side on a single substrate, and can be used on different layers of a substrate either together alone, can be used on different substrates that are coupled to a single or multiple coils of elements 10.

Figure 50:
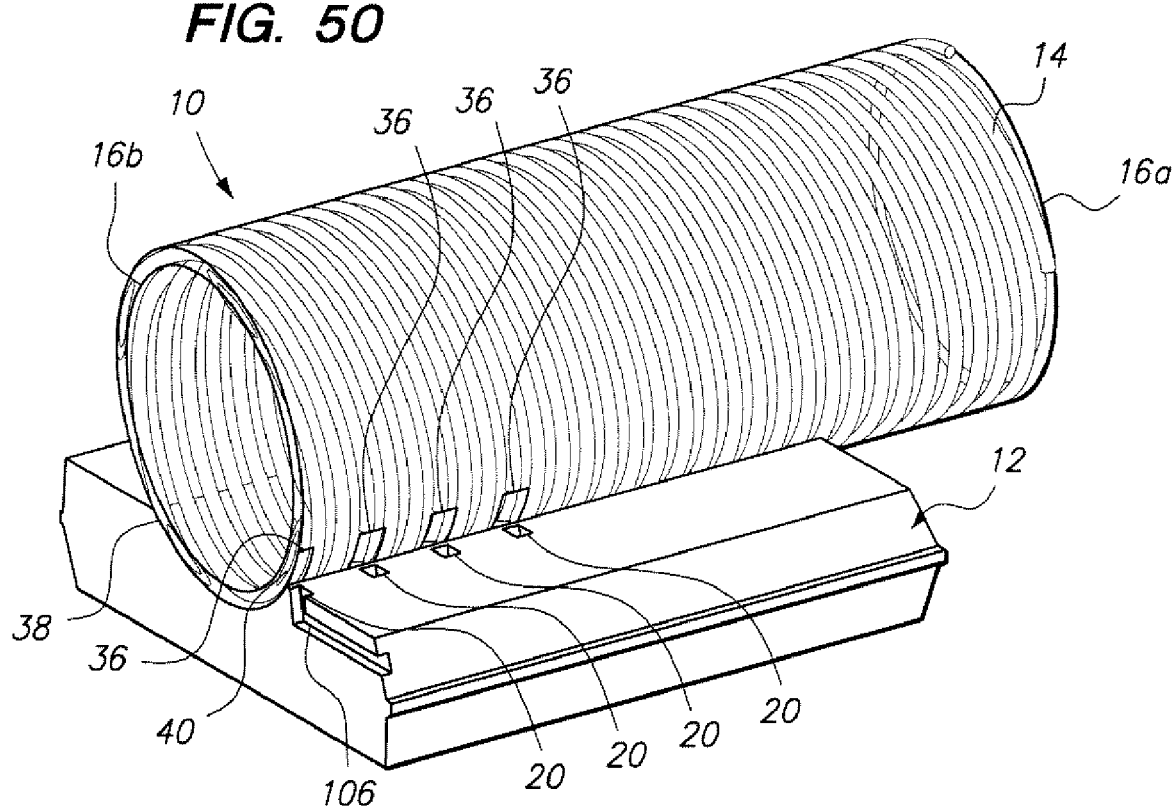
FIG. 50 is a perspective view of a fifteenth example system, representing a fluidic structure.

FIG. 50 shows a substrate 12 with a coil 10 disposed in opening 38 therein. The substrate 12 has channels 106 formed inside and filled with a removable material. On the surface of the substrate 12 are contact pads 20 which are also made of a removable material. Selected tubes 14 within the coil 10 are filled with a removable material and have stripped areas 112 which expose the removable material inside the tubes 14.

Figure 51:
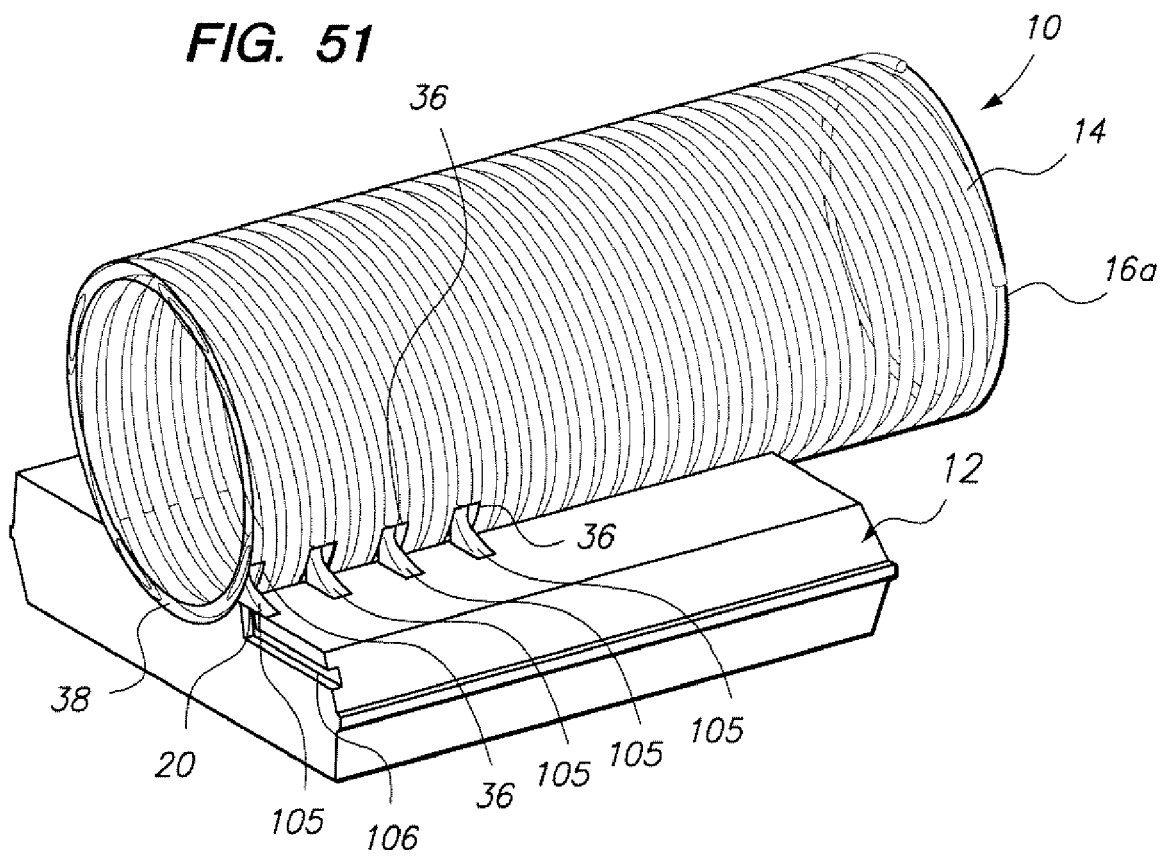
FIG. 51 is a perspective view of the example system of FIG. 50 with a dissolvable material applied.
Figure 52:
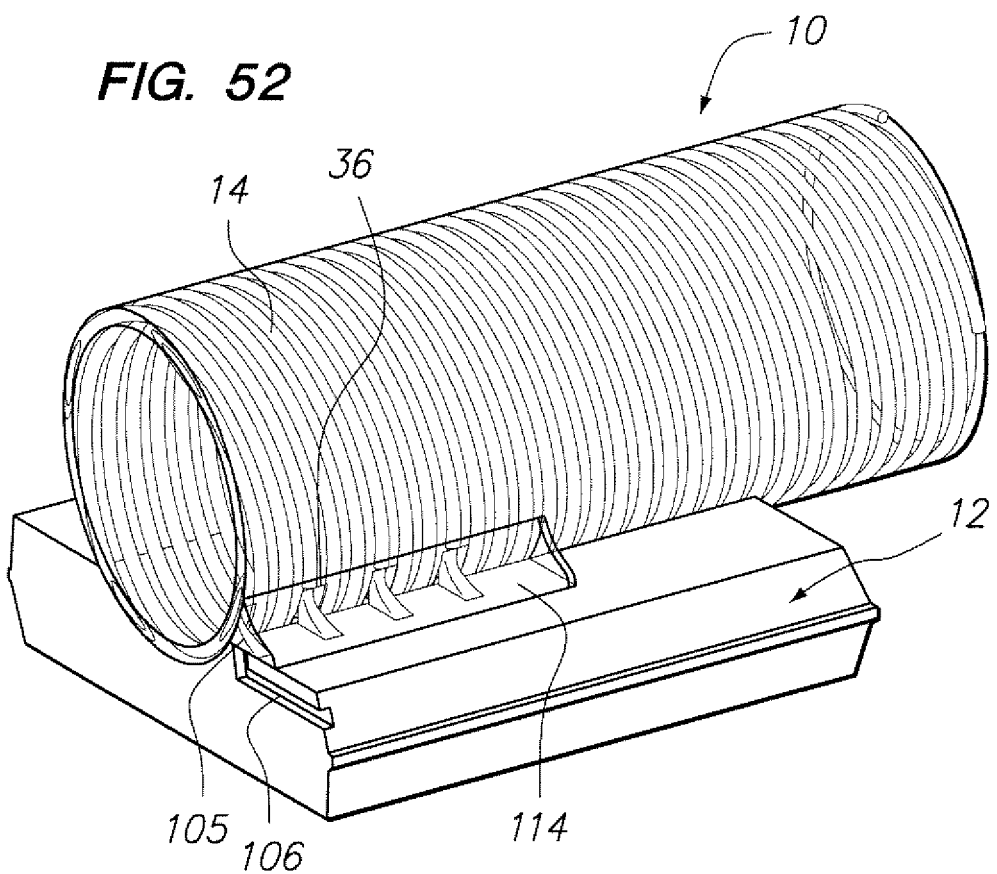
FIG. 52 is a perspective view of the example system of FIG. 51.

FIG. 51 depicts a removable connection material 105 between the wire cores 40 and connection pads 20. The connection material 105 forms part of the mechanical envelope of the transfer passage 107. In FIG. 52, attachment material 114 is added between the tubular structure 16 and the substrate 12 in order to mechanically restrain the coil 10 and to form the other part of the mechanical envelop of the transfer passage 107 that transfers fluid from the tube 14 to the channel 106.

Figure 53:
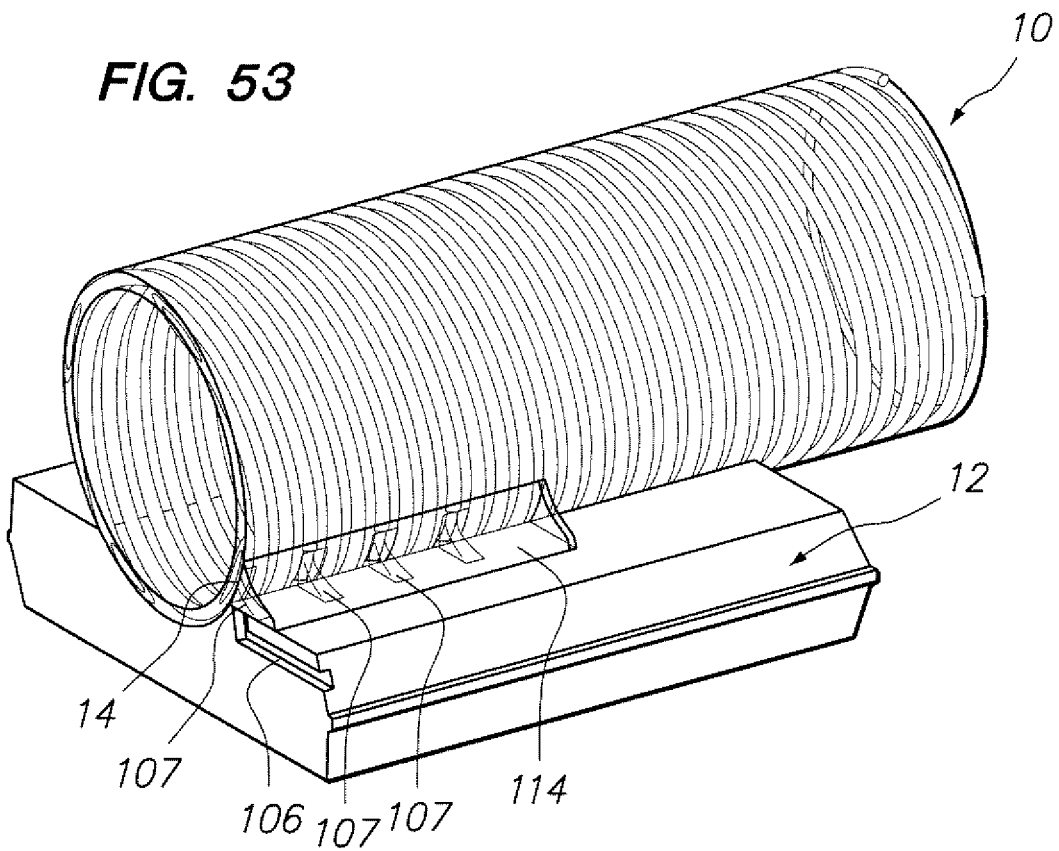
FIG. 53 is a perspective view of the example system of FIG. 52 after the dissolvable material is removed.
Figure 54:
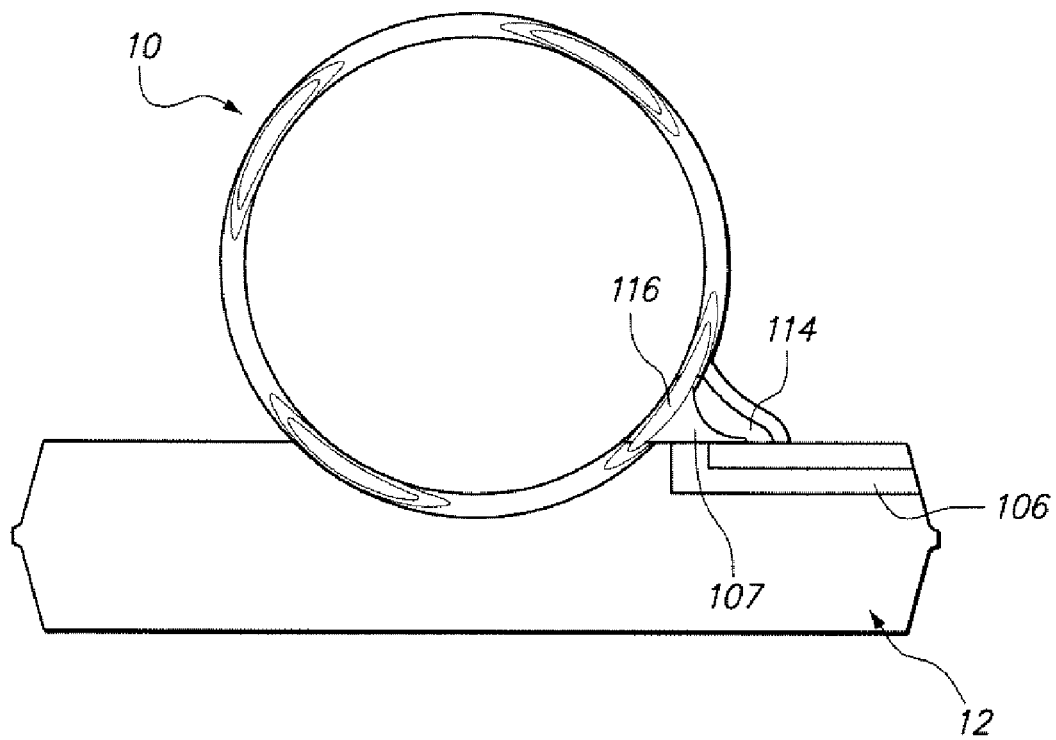
FIG. 54 is a cross-sectional view of the example system of FIG. 52.
Figure 55:
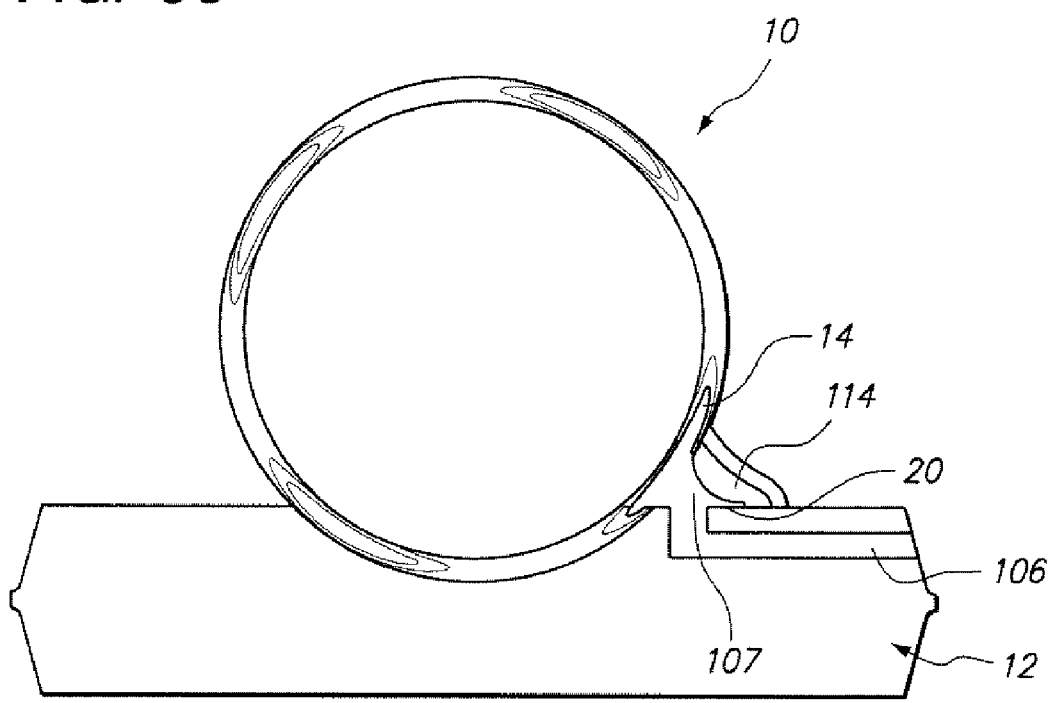
FIG. 55 is a cross-sectional view of the example system of FIG. 53.

In FIG. 53, the removable material is removed from the system. This leaves hollow channels 106 inside the substrate 12, a hollow transfer passage 107 and hollow wires or tubes 14 in the coil 10. In FIG. 54, a section view through one of the connection pads 20 shows a section of the channel 106 in the substrate 12 being filled with a removable material and another removable material forming a transfer passage profile 107 and a third removable material 116 inside the tube 14. Thus the path from the coil 10 to the substrate 12 is clearly shown. In FIG. 55, a section view through one of the connection pads 20 shows a section of the system after all the removable material has been removed. This leaves transfer passage 107 empty and allows for the flow of material through the channel 106.

Any given wire with a coil may also contain a dissolvable core. This allows for a very low cost way of integrating massively multi lumen catheters with electrical connections. Such a system is shown in FIGS. 50-55. The tubular structure shows only a single wire for clarity but it is to be understood that a plurality of wires 14 can also exist within such a system. The wire is then stripped of its insulation 112, but left mostly intact both in the containing insulation and in the tubular wall structure. The stripped wire portion is then aligned on the dielectric substrate 12 over the connection pad 20 and a temporary gusset 105 is formed between the wire core and the contact pad 20. The contact pad 20 and gusset material 105 are also formed out of dissolvable material such that when the material is removed, a channel 106 will exist between the dielectric substrate 12 and the tube within the tubular structure. Before the gusset and associated materials are dissolved, a final covering material 114 is used to completely encapsulate the original gusset and retain the tubular structure. The channel 107, 106 inside the dielectric substrate 12 can also be easily attached to a micro-fluidic controller or some other such system. With the material removed; fluids, particulates, gasses, cryogens, and combinations thereof can flow from the tip of the catheter down to the dielectric substrate 12 and vice versa. This allows for activities like drug delivery, blood sampling, and other important activities.

Dissolvable Cores to Create Transfer Passages: Transfer Passages 107 are the fluid equivalent of a solder joint. They are a passageway extending from the stripped and opened center of the tube 116 disposed in a helical fashion around the body of the catheter to the opening 20 over the channels 106 inside the 2 D structure 12.

When the material inside the tube 14 is dissolved, a hollow transfer passage 107 is formed between the channel 106 in the substrate 12 and the hollow lumen 116 within the tubular structure 10. Thus a transport system is formed from the micro fluidic channel or channels contained in the substantially 2D structure 12 continuously through to the tubes or lumens in the wall of the 3D structure 10.

The channels thus formed inside the substrate 12 can be easily attached to micro fluidic controllers, reagent cavities or can be routed to more macro scale tubing systems, hydraulics, or other such system. After the core of such a wire 14 has been dissolved, the remaining tubular structures 10 can be used with micro fluidic devices to allow for reagent mixing, drug delivery, blood sampling, saline delivery, drainage, controlled cryogenic delivery and extraction, as well as a number of other uses. With the material removed; semi-solids, particulates, fluids, cryogens, gasses, and combinations thereof can flow from the tip of the 3D tubular structure down to the 2D dielectric substrate 12 and vice versa.

Minimally invasive surgical procedures rely on being able to do a lot of work while causing the patient less pain, scarring, and lower recovery times. This is commonly accomplished by making a small artificial incision and feeding a tube up through the incision and having all of the instrumentation needed fed up through the tube. Modern catheters feed wires up through the body of the tube to tips on the catheters which can be used to diagnose and treat a multitude of disorders. Being able to go home directly after a surgical procedure is considered more desirable then long hospital stays. As such, there is an ever growing demand for new procedures and hence for new micro medical devices. Designers are working at a cross purpose though; in order to create a less traumatic experience, a smaller catheter body is desired. To allow for more complex procedures, more wires are needed inside the catheter, pushing for larger catheter bodies. Catheter bodies are not always round and are not always tubes. Ovoid shapes are very popular as they allow for easier bending in certain directions, which makes steering the catheter easier in certain situations. Catheters can also contain a number of different "tubes" or lumens that have been all formed at the same time. Typically, certain lumens are used to carry wires and other lumens are used to carry fluids.

Fluid transportation is useful for a variety of reasons. One reason is for drainage, much like what a dentist does with excess saliva except integrated into the same tool being used to clean your teeth. Another reason is for sampling of whatever the tip is interacting with, so you could have real time localized blood oxygen content readings as well as measuring what other chemicals are present in the blood stream during surgery. Tubes can also be used to push material into the area as well as to take materials away from the area. Saline, being both neutral to the body and conductive, is often used during ablation procedures. Drugs can also be delivered along the same channels and allow for very specific targeting of problem sites.

Cryogens can also be sent up the tube to freeze off a very small portion of the body. Many people have warts frozen off from external body parts because it is a very effective method of killing off a localized area in a way that the body quickly repairs. Being able to freeze interior portions of bodily anatomy could easily revolutionize current cancer treatments.

Instead of running wires inside of a tubular structure as separate elements, we have developed a method of integrating the wires into the very structure of the tube. Moving the wires into the tube wall frees up the lumens for other purposes. Having wires run parallel to the axis of the tubular structure may be easier to manufacture, but it presents difficulties in that it tends to make the resulting tubular structure more rigid. By wrapping the wires around the tubular structure in a coil or a more helical pattern, flexibility can be increased and subsequent work hardening of the wires is greatly reduced. Varying the pattern allows for different levels of stiffness or rigidity at different points along a tubular structure, in effect replacing complex multi durometer tubular structures. Helical coils also allow for some interesting termination options. Fiber optics can be split, with only minimal impact on signal integrity by matching up helical tangents on two different tubular structures. Helixes will also eventually cause all the conductors in a system to pass through a single tangent line parallel to the axis of the tubular structure, thus allowing for easy attachment of multiple wires to a single line on a single substrate. This also allows for adding in electrical connections to devices and structures that would otherwise not contain them. For example wires could be wrapped around a fiber optic element. Though separately insulated wires are easy to incorporate, it is also easy to use flex circuits or otherwise added conductive material, by such common processes as sputtering, to the outside of a tubular structure.

Tubular structures need not apply only to medical catheters. Tubular structures are used in everything from avionics to architecture. Being able to have a high density interconnection system that still allows for structural rigidity and/or allows for other devices to share the same space is of great use in a variety of industries. For example, airplanes could move most of their wiring harnesses to the skin of the airframe using the herein described techniques. Also, power conduits and network connections could run up a central structural member of a new building and could use the herein described technology to run high density backbones between floors.

Figure 56:
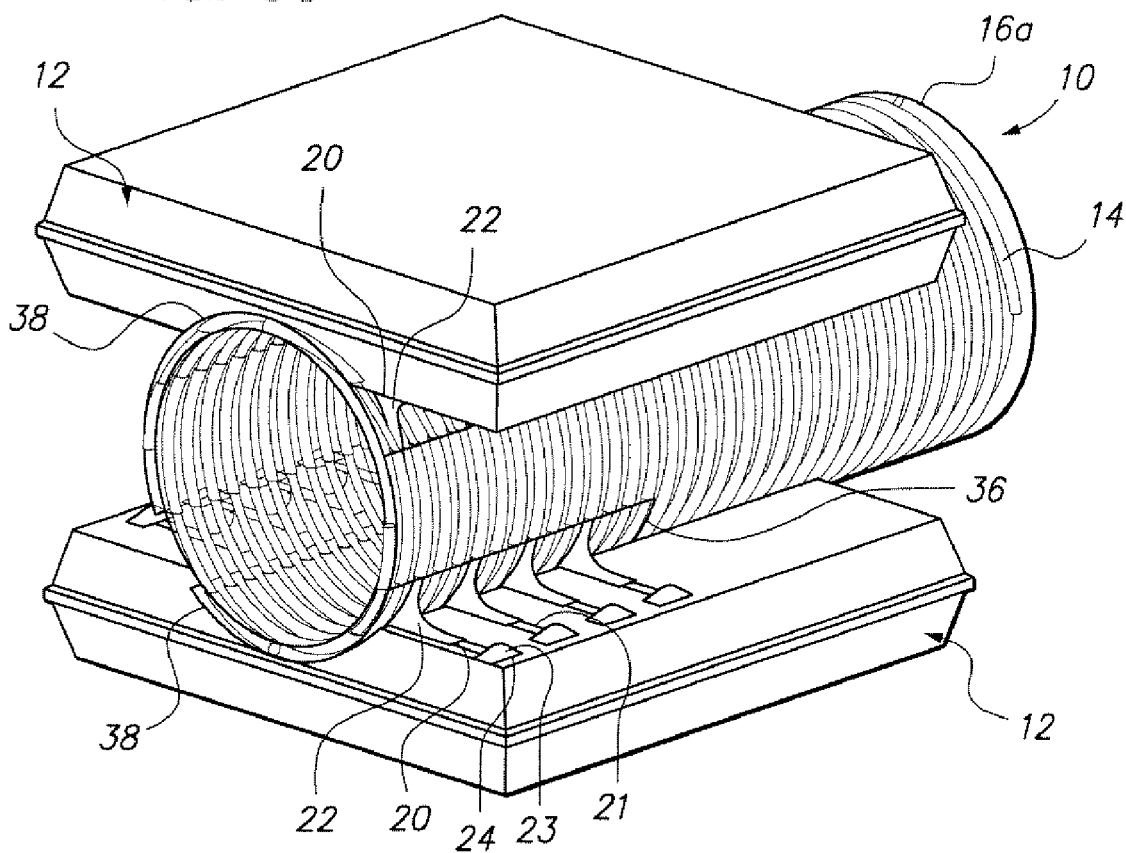
FIG. 56 is a perspective view of a sixteenth example system.
Figure 57:
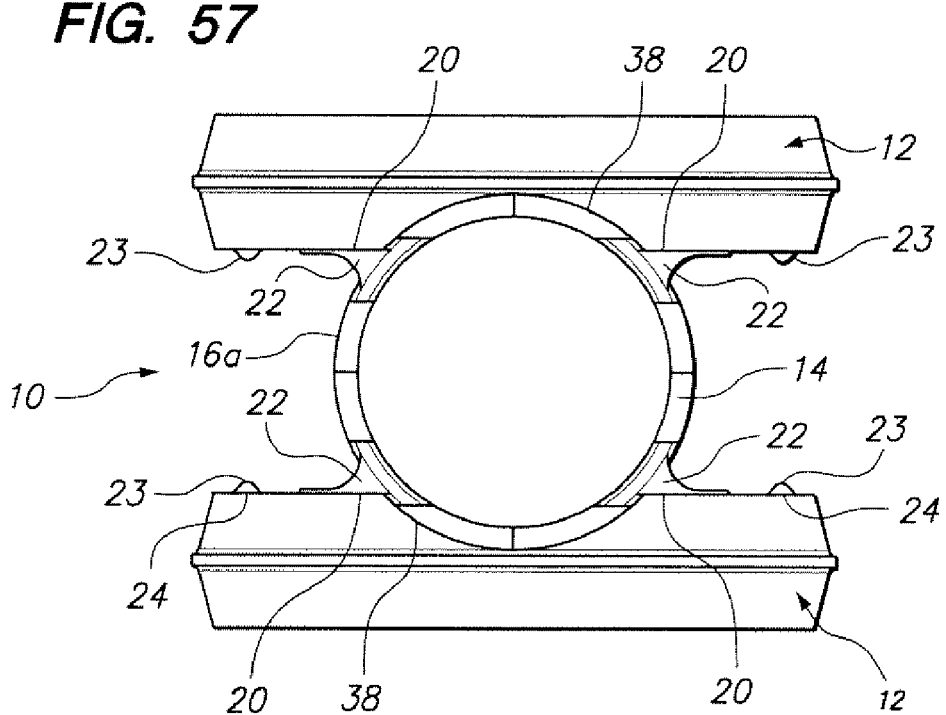
FIG. 57 is a cross-sectional view of the sixteenth example system.

FIGS. 56 and 57 depict an alternative example where the coil of elements 10 is sandwiched between two dielectric substrates 12. In this example, as with the prior examples, the coil of elements 10 can be coupled to surfaces on both dielectric substrates 12. As shown in FIG. 57, the coil of elements 10 is coupled to the lower dielectric substrate 12 utilizing retention solder 22 positioned on a contact pad 20. In addition, a heat transfer pad 24 for thermally communicating with the contact pad 20 and connection solder 22 is disclosed. In addition, the coil of elements 10 is coupled to the upper dielectric substrate 12 on the bottom surface 32 thereof in a similar manner. Both substrates 12 include a recess 38 for receiving at least a portion of the coil of elements 10 therein. FIGS. 56-57 show another example of how a single tubular structure can connect to multiple dielectric substrates 12.

Figure 58:
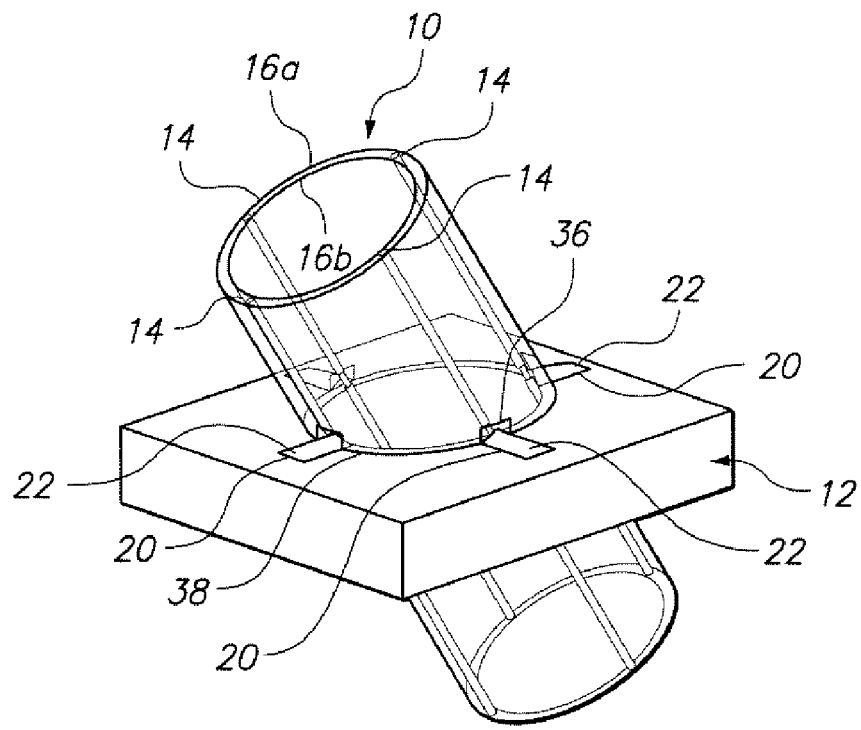
FIG. 58 is a perspective view of a seventeenth example system.
Figure 59:
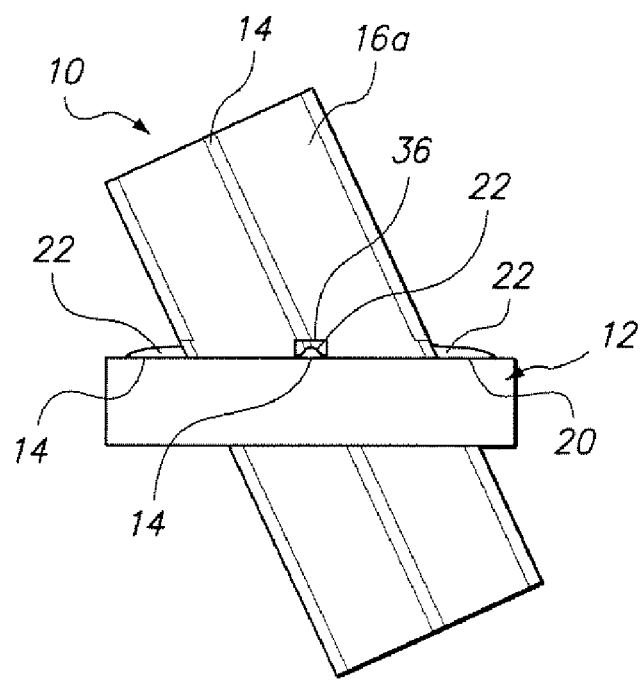
FIG. 59 is a side elevation view of the example system of FIG. 58.

FIGS. 58 and 59 disclose an example similar to that in FIGS. 11 and 12, except for the coil of elements 10 in FIGS. 58 and 59 is positioned at an angle relative to the surface 28 of the dielectric substrate 12. The hole or passageway 38 that is defined through the dielectric substrate 12 is similarly angled such that the coil of elements 10 is able to rest within the hole that is defined in the dielectric substrate 12. The coil of elements 10 can be positioned at any angle relative to the surface 28 of the dielectric substrate 12 including a 45° angle, a 60° angle, 80° angle or perpendicular to the dielectric substrate 12 among other angles, the disclosure not being limited to a particular angle of the coil of elements 10 relative to the surface 28 of the dielectric substrate 12. The connections between the wires 14 of the coil of elements 10 and the contact pads 20 and connection solder 22 disposed on the surface of the dielectric substrate 12 are similar to that previously discussed in connection with FIGS. 11 and 12.

FIGS. 58-59 illustrate the advantage of the mounting hole 38 not being perpendicular to the dielectric substrate 12. As the tubular structure 10 and the dielectric substrate 12 depart from a right angle, the connection material 22 is placed more and more in shear when axial load is placed on the tubular structure 10, thus increasing the overall strength of the adhesion between the dielectric substrate 12 and the tubular structure 10.

Figure 60:
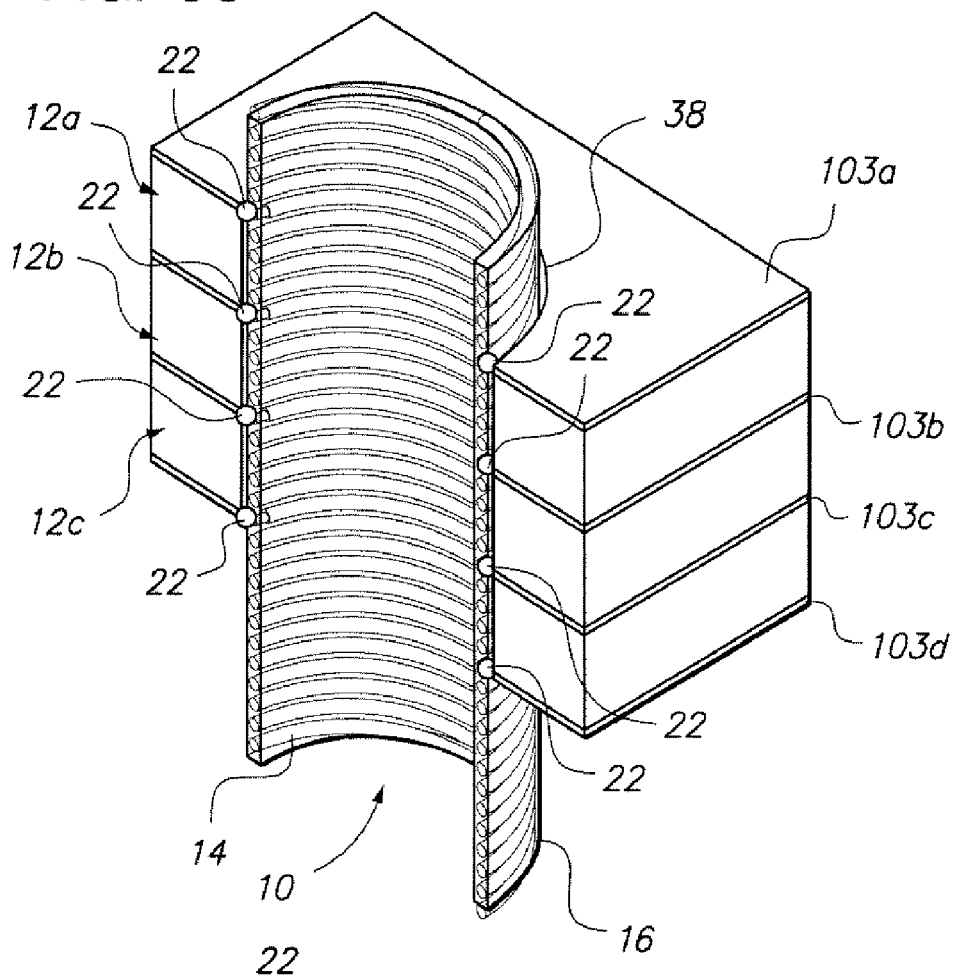
FIG. 60 is a cross-sectional perspective view of a seventeenth example system.
Figure 61:
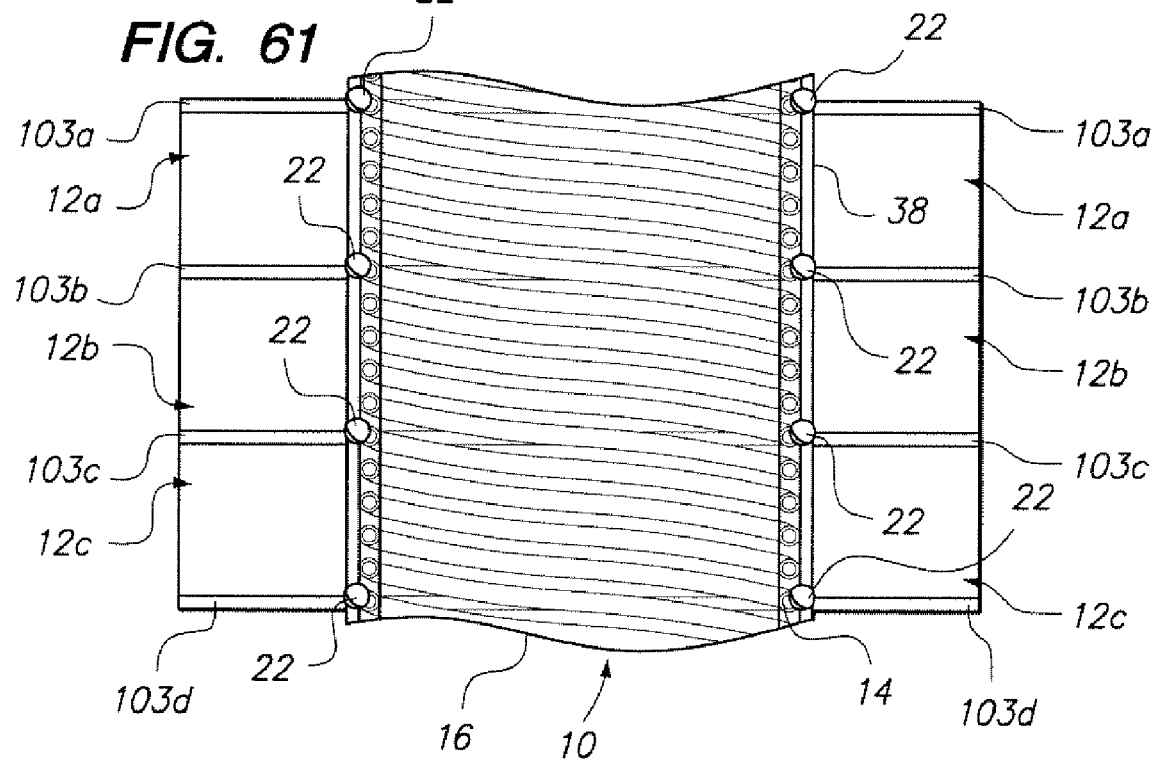
FIG. 61 is a side view of the example system of FIG. 60.

FIGS. 60-61 show how multiple substrates can be laminated together, each with their own connection pads 20 disposed around a common mounting hole 38, and contact a tubular structure 10 having wires 14. This allows for easy integration of soldered and non-soldered joints in a very compact environment. In one example, the connection pads are formed from conductive layers 103 similar to those found in common multilayered printed circuit board substrates. Regardless of the substrate used, the connection pads 103a-103d all have connection material 22 disposed along an edge thereof using a variety of reflow methods. The wires 14 within the tubular structure are then selectively stripped of their insulation 26 and inserted within the hole 38. Optionally, the tubular structure 10 is press fit into the hole 38 for added mechanical retention. Once inserted, the contact pads 103a-103d are heated, either through resistive heating between another contact point along the wire and the contact pad or through other heating methods, and the connection material 22 melts and attaches to the wire core 40 in a manner similar to the ones described above.

The substrate 12 can be prepared by forming a groove 38 in a planar surface of the substrate 12. The groove 38 is sized and configured to receive a portion of the coil 10 along its axial length. Conductive material 103 is applied to the planar surface of the substrate 12 during the initial manufacture of the substrate 12 at a spacing that matches an even increment of the wires 14 within the coil 10. The conductive material 22 forms a plurality of connection pads 103a-103d which are usually disposed perpendicularly to the axis of the groove 38 and abut the edge of the groove 38. Each connection pad 103a-103d may be surrounded by a secondary dielectric 100 (shown in FIG. 1) in order to prevent connection material 22 from flowing over the surface of the substrate 12 in an uncontrolled manner. The connection material 22 is added on top of connection pad 103 to enable the electrical and mechanical joining of the substrate 12 to the wire 14 and hence mechanically retain the coil 10 and allow for electrical communication between a distal end of the coil 10 and the substrate 12. The connection material 22 is added before the coil is introduced but after the formation of the groove 38 but the connection material 22 can also be added at the same time as the coil 10 is aligned inside the groove 38 with the connection pads 103a-103d. Also, the connection material 22 would be added in an automated manner, such as with a solder stencil and reflow process standard to the electronics industry.

The coil 10 is prepared by removing portions of the tubular structure 16 in the area where the wires 14 are to be soldered to the substrate 12. Furthermore, each wire 14 that is to be attached has some of its insulation 26 removed at that location. Wires 14 can be stripped using a laser cutting or other technique, such as, but not limited to, thermal ablation, chemical etching, and bead blasting. Both the tubular structure 16 and the wire insulation 26 are ideally removed at the same time and only in the locations needed to attach a wire 14 to a connection pad 103. The wire 14 can be tinned, before or after the insulation is removed, with a coating of connection material 22 to facilitate attaching the wire 14 to a connection pad 103.

In order to attach the coil 10 to a substrate 12, the coil 10 is placed within the groove 38 and each wire 14 to be affixed is aligned with a respective connection pad 103. Because the conductive material 103 was placed at an even increment of the pitch of the wires 14, only a single wire 14 has to be aligned with a pre-determined connection pad 103 and all other wires 14 will be aligned with their respective connection pads 103. This saves time during assembly and eases the process of soldering multiple wires 14 to a substrate 12.

Each stripped wire 14 is attached to a respective connection pad 103 with an individual connection material 22. Specifically, a heat source is placed in thermal communication with connection pad 103. The heat then travels through the connection material 22 and is transferred to the wire 14. The connection material 22 then wicks up the heated wire 14 forming a joint between a connection pad 103 and the wire 14. Once the thermal communication is taken away, the connection material 22 hardens thus securing the wire 14 to the connection pad 103 and, hence, to the substrate 12 and any other components or structures that may be in electrical communication with the underlying conductive material 103.

Additionally, it is possible to attach wire 14 to connection pad 20 using a heat transfer technique. In this instance, the heat from a given source, typically a soldering iron, is applied to a heat transfer pad 24 which is in thermal communication with a connection pad 20. The heat transfer pad 24 is in communication with the contact pad 20 such that connection material 22 can be melted without physical contact from the original heat source. A secondary dielectric 21 may be placed between the heat transfer pad 24 and the connection pad 20 in order to prevent the cross contamination with the connection material 22 disposed on the surface of the connection pad 20. A secondary bump of connection material 23 can be added on top of the heat transfer pad 24 to aid in the thermal communication between a heat source and the heat transfer pad 24 and hence between a heat source and the connection material 22 and from there to the wire 14.

Discontinuous Structures: By using a process that adds wires or other such conductive elements selectively, it is possible to have wires go only partway down a tubular structure. This means that there can be arbitrary segments of the tubular structure that contain a different number of wires 14 then other portions. It is also possible to run all the wires 14 down the length of the tubular structure but to cut, or otherwise splice, certain wires 14 at a given point, effectively turning a single wire into two electrically separate pieces. Having a different number of wires 14 means that the apparent flexibility of the system can be further refined. However, a more ingenious use of the system is to add in a "backplane" type interconnect system between multiple substrates 12 attached to the coil. Not only does such a backplane, or perhaps more properly a "frontplane", drastically simplify routing difficulties, but it can also lower the cost of the substrates by allowing for fewer interlayer connections or vias. Each wire in the frontplane can be used to carry a different type of information. Electrical signals, light impulses, power connections, fluid samples, gaseous reagents, and many others can be moved from substrate 12 to substrate 12, either individually or en masse, and from any given substrate 12 to locations further down the tubular structure.

An optional method of attaching the wires 14 in a coil 10 to a substrate 12 that allows for redundancy for safety, mechanical stability, and an increased coil density while simultaneously easing the assembly process is seen in FIG. 34. Each instance of conductive material 22 is labeled either "1", "2", "3" or "4" for ease of illustration. It can be seen that wire 14*d* is aligned and attached to connection pad 20*d*, wire 14*c* is aligned and attached to connection pad 20*c*, wire 14*b* is aligned and attached with connection pad 20*b*, and wire 14*a* is aligned and attached with connection pad 20*a*. Each of the labels then shows and identifies each wire 14 from the coil 10 as a separate joint and makes it easy to identify. It will be recognized by those of ordinary skill in the art, that any wire 14 can be soldered to the substrate 12 at multiple locations using the techniques described herein and that any number of wires 14 can be attached to a substrate 12 with these techniques.

A method is disclosed for transporting a fluid, gas, semi-solid, cryogen, or particulate matter between a three dimensional structure 10 and a substantially two dimensional structure 12. The method includes a step of providing a hollow member 14 having a removable material disposed therein. The hollow member 14 is associated with a three-dimensional structure 10 associated with an electrically conductive element, a fluidically conductive element, or a combination thereof. Another step entails associating the hollow member 14 with a hollow transfer passage 107 of a substantially two-dimensional structure 12. Another step entails covering the hollow member 14, and at least one of the two-dimensional structure 12 and the three-dimensional structure 10 with a substance. Yet another step entails removing the removable material 116 to define a passage in communication with the hollow transfer passage 107 of the substantially two-dimensional structure 12 and the hollow member 14 of the three-dimensional structure 10.

The method may further include removing part 26 of the hollow member to expose the removable material 116 before applying the substance. It further includes associating the exposed removable material of the hollow member 14 to the hollow transfer passage 107 of a substantially two-dimensional structure 12, wherein the substance is utilized to cover the exposed removable material to define a passage between the hollow member 14 and the hollow transfer passage 107.

The substantially two-dimensional structure 12 is coupled to one or more dielectric substrates 12, with a fluid passage 106 defined through the dielectric substrates 12 in communication with the hollow transfer passage 107. A fluid, gas, semi-solid, cryogen, or particulate matter is transported from the hollow member 14, through the substance, through the hollow transfer passage 107, to the fluid passage 106.

A system for transporting a fluid, gas, semi-solid, cryogen, or particulate and for establishing a fluidic or hollow connection between two structures includes the following: A three dimensional structure 10 has a plurality of conductive elements 14 associated therewith, the conductive elements 14 each having a channel for transporting materials therealong. A removable material 116 is disposed within the channel of the conductive elements 14 and coupled to the substantially two-dimensional structure 12, the removable material 116 being covered with a substance such that when the material is removed, a hollow transfer passage 107 is defined. The substance mechanically connects one of the conductive passageways 106, 107 in the substantially two-dimensional structure 12 to the passageways in the three-dimensional structure 10.

The two-dimensional structure 12 can contain multiple layers for the transfer of multiple media and materials. The three dimensional structure 10 further includes conductive elements 14 that have a conductive member 40 disposed therein for establishing an electrical connection with the two-dimensional structure 12.

A system for electrically coupling a three dimensional structure 10 to a substantially two-dimensional structure 12 includes a three-dimensional conductive structure and a substantially two-dimensional conductive structure. It further includes a means for electrically coupling the substantially two dimensional conductive structure to the three-dimensional conductive structure along an attached section while maintaining flexibility of the attached section and promoting mechanical retention of the three dimensional structure 10 to the two dimensional structure 12.

The three-dimensional conductive structure 10 is tubular and the two-dimensional structure 12 has a passageway 38 defined therein for accepting at least part of the three-dimensional conductive structure 10.

A system for electrically coupling a three dimensional structure 10 to a substantially two-dimensional structure 12 includes a tubular coil of conductive elements 14 that are selectively electrically isolated from one another. A dielectric substrate 12 is sized and shaped to come into proximity with at least a portion of the tubular coil 10. A connection pad 20 has a connection material 22 disposed thereon positioned on the dielectric substrate 12. The connection material 22 is for coupling the conductive elements 14 to the dielectric substrate 12.

The connection pad may be a conductive contact pad 20 coupled to a surface of the dielectric substrate 12 and the connection material 22 is a thermally activated conductive connection material 22 for coupling a conductive element from the tubular coil to the connection pad 20.

A system for electrically coupling a three-dimensional structure 10 to a substantially two-dimensional structure 12 includes the following: A three-dimensional structure 10 has a plurality of conductive members 14 extending along a length thereof, said plurality of conductive members 14 being selectively electrically isolated from one another. A dielectric substrate 12 is sized and shaped to come in proximity with at least a portion of said three-dimensional structure 10 to mechanically and electrically couple the conductive members 14 of the three-dimensional structure 10 to the dielectric substrate 12. A connection pad 20 has a connection material 22 disposed thereon positioned on the dielectric substrate 12. The connection material 22 is for coupling the conductive elements 14 to the dielectric substrate 12.

The connection pad may be a conductive pad 20 coupled to the dielectric substrate 12, and the connection material 22 is a conductive material disposed on the conductive pad 20. The three dimensional structure 10 comprises a coil of wires. The three dimensional structure 10 comprises a flex circuit. The dielectric substrate 12 is a printed circuit board and the connection material 22 is a solder. The connection pad 20 on the dielectric substrate 12 is formed as a substantially two dimensional structure 12. The system further comprises a heat transfer pad 24 in thermal communication with the connection pad 20. The coil of wires 14 includes multiple conductors.

Also, the three-dimensional structure 10 may include at least one inner sheath 16b and an outer sheath 16a, with a plurality of wires 14 disposed between the inner and outer sheaths 16b, 16a. A hole 36 is cut into the outer sheath 16b at a connection point where one of the conductive elements 14 within the tube 10 is coupled to the connection pad 20 with connection material 22 The wires 14 have a protective coating 26 that is stripped away in the vicinity of the hole 36 that is cut into the outer sheath 16a. The three-dimensional structure 10 is hollow. The coil of wires 14 further includes tubes which can transmit semi-solids, particulates, gases, cryogens, and fluids.

Also, a plurality of three-dimensional structures 10 are coupled to a single two-dimensional structure 12. A plurality of two-dimensional structures 12 are coupled to a single three-dimensional structure 10. The two-dimensional structure 12 is part of a printed circuit board. Connection pads 20 and connection material 22 are disposed on both sides of the printed circuit board, with the printed circuit board having a hole 38 disposed therethrough for receiving the three-dimensional structure 10 such that the three-dimensional structure 10 is coupled to both sides 28, 32 of the printed circuit board at the connection pads 20 via the connection material 22. The two-dimensional structure 12 is part of a printed circuit board and has four corners, with portions of each corner being cutaway to reveal passageways 38 for receiving the three-dimensional structure 10 therein. The two-dimensional structure 12 is part of a printed circuit board. A groove 38 is disposed in the printed circuit board for receiving a three-dimensional structure 10 therein.

Each wire 14 is stripped of its insulation at the locations of the connection pads 20. Connection material 22 attaches the wire 14 to the contact pad 20. The connection material 22 creates a bump that flows over the stripped wire 14. As seen in FIG. 38, only one wire 14 is attached to the substrate 12 at a given section.

Two wires 14 can be attached to the substrate 12 on opposing sides of the tubular structure 16. By varying the spacing of wire 14 along the tubular structure 16 and hence along the coil 10 and stripping wires 14 of their insulation at desired locations, it is possible to attach only certain wires 14 at certain locations very easily and very accurately.

In addition to the foregoing, it is also possible to attach wires 14 inside a tubular structure 16. A small substrate 12 is placed within the tubular structure 16. The substrate 12 has connection pads 20 with connection material 22 formed thereon. Wires 14 can then be attached to the substrate 12 using any known method.

The coil 10 may be comprised of a flat flexible substrate (not shown) upon which is disposed a conductive material such that there are exposed areas and covered areas along the conductive materials path. The end of the flexible material is folded under itself, exposing the exposed conductive material all along the outside of radius. With the exposed conductive material displayed in such a manner, it becomes very easy to both mechanically and electrically attach flexible material to connection pad with conductive material. The conductive path thus formed can be easily used to connect components 30 to the coil 10 with conductive material disposed on the substrate.

It is not necessary to connect the coil 10 to something directly on the substrate 12. Specifically, substrate 12 can be so configured such that mounting pads 20 match corresponding pads on either another substrate 12 or a Flex Circuit, or even Pogo Pins.

A substrate 12 can become a connector in and of itself. When a plurality of pins protrude through or from one of the surfaces of the substrate 12 and are in electrical communication with conductive material, then pins can be easily arranged in such a fashion as to mate with a receptacle that can then carry an electric current to another device or devices. It is to be understood that the previous examples are just that: examples; and that the underlying termination technology can be expanded and incorporated into other electrical and electromechanical devices.

The term "substantially" is used herein as a term of estimation.

It will be appreciated by those of ordinary skill in the art that the concepts and techniques described herein can be embodied in various specific forms without departing from the essential characteristics thereof. The presently disclosed examples are considered in all respects to be illustrative and not restrictive. The scope of the invention is indicated by the appended claims, rather than the foregoing description, and all changes that come within the meaning and range of equivalents thereof are intended to be embraced.

What is claimed:

1. A system for electrically coupling a three-dimensional structure to a substantially two-dimensional structure comprising:
   an elongated three-dimensional structure having a plurality of separate conductive elements extending along a length thereof to define a coil, the conductive elements being electrically isolated from one another within the coil, providing the coil with a cross-sectional periphery shaped as a plane figure, and having attachment portions at said cross-sectional periphery of the coil;
   a dielectric substrate having a substantially two-dimensional portion sized and shaped to come in proximity with the attachment portions of the conductive elements at connection points adjoining said cross-sectional periphery of the coil; and
   a plurality of connection pads located on the substantially two-dimensional portion of the dielectric substrate and having connection material disposed thereon at the connection points for coupling the conductive elements to the dielectric substrate;
   wherein the three-dimensional structure includes inner and outer sheaths, the conductive elements are wires disposed between the inner and outer sheaths, holes are formed through the outer sheath at the attachment portions, and each wire has a protective coating that is removed in the vicinity of a hole in the outer sheath.

2. The system of claim 1, wherein the connection pads are conductive pads coupled to the dielectric substrate and the connection material is solder.

3. The system of claim 1, wherein the dielectric substrate is a printed circuit board and the connection material is solder.

4. The system of claim 1, further comprising a heat transfer pad in thermal communication with a connection pad.

5. The system of claim 1, wherein the three-dimensional structure is hollow.

6. The system of claim 1, wherein the three-dimensional structure is one of a plurality of three-dimensional structures coupled to the dielectric substrate.

7. The system of claim 1, wherein the dielectric substrate is part of a printed circuit board, and connection pads and connection material are disposed on both sides of the printed circuit board, with the printed circuit board having a hole therethrough for receiving the three-dimensional structure such that the three-dimensional structure is coupled to both sides of the printed circuit board at the connection pads via the connection material.

8. The system of claim 1, wherein the conductive elements have helical sections that include the attachment portions.

9. The system of claim 1, wherein the conductive elements have linear sections that include the attachment portions.

10. The system of claim 1, wherein the attachment portions of the conductive elements are spaced apart around the periphery of the coil.

11. The system of claim 1, wherein the attachment portions of the conductive elements are spaced apart along the length of the coil.

12. The system of claim 1, wherein the substantially two-dimensional portion of the dielectric substrate is an upper or lower surface of the dielectric substrate.

13. The system of claim 1, wherein the coil extends through a through-hole in the dielectric substrate.

14. The system of claim 13, wherein the dielectric substrate has opposite side surfaces in parallel planes, and the through-hole extends through the dielectric substrate at an acute angle to the opposite side surfaces.

15. The system of claim 1, wherein the coil extends through a cut-out at a corner of the dielectric substrate.

16. The system of claim 1, wherein the coil has an end abutting a surface of the dielectric substrate.

17. The system of claim 1, wherein the coil extends lengthwise across a surface of the dielectric substrate.

18. The system of claim 17, wherein the coil is received in a recess extending across the surface of the dielectric substrate.

19. The system of claim 1, wherein the three-dimensional structure is tubular.

20. The system of claim 1, wherein the plane figure is a circle.

21. The system of claim 1, wherein the plane figure is a polygon.

22. The system of claim 1, wherein the plane figure is a rectangle.

23. The system of claim 1, wherein the plane figure is a square.

24. The system of claim 1, wherein the plane figure is a triangle.

25. The system of claim 1, wherein the plane figure is an oval.

* * * * *